US00RE47404E

(19) United States
(12) Reissued Patent
Rossignol

(10) Patent Number: US RE47,404 E
(45) **Date of Reissued Patent: *May 28, 2019**

(54) VIRAL HEPATITIS TREATMENT

(71) Applicant: Romark Laboratories, L.C., Tampa, FL (US)

(72) Inventor: Jean-Francois Rossignol, St. Petersburg, FL (US)

(73) Assignee: ROMARK LABORATORIES, L.C., Tampa, FL (US)

( * ) Notice: This patent is subject to a terminal disclaimer.

(21) Appl. No.: 15/644,637

(22) Filed: Jul. 7, 2017

Related U.S. Patent Documents

Reissue of:
(64) Patent No.: 9,107,913
Issued: Aug. 18, 2015
Appl. No.: 14/137,280
Filed: Dec. 20, 2013

U.S. Applications:
(63) Continuation of application No. 11/651,672, filed on Jan. 9, 2007, now Pat. No. 8,633,230.

(60) Provisional application No. 60/757,036, filed on Jan. 9, 2006.

(51) Int. Cl.

| | |
|---|---|
| ***A61K 31/425*** | (2006.01) |
| ***A61K 38/00*** | (2006.01) |
| ***A61K 31/70*** | (2006.01) |
| ***A61K 31/426*** | (2006.01) |
| ***A61K 31/7068*** | (2006.01) |
| ***A61K 38/21*** | (2006.01) |
| ***A61K 45/06*** | (2006.01) |

(52) U.S. Cl.
CPC ..... *A61K 31/426* (2013.01); *A61K 31/7068* (2013.01); *A61K 38/21* (2013.01); *A61K 38/212* (2013.01); *A61K 45/06* (2013.01)

(58) Field of Classification Search
CPC ..... A61K 31/426
USPC ..... 514/370
See application file for complete search history.

(56) References Cited

U.S. PATENT DOCUMENTS

| | | | |
|---|---|---|---|
| 3,950,351 | A | 4/1976 | Rossignol et al. |
| 3,957,812 | A | 5/1976 | Rossignol et al. |
| 4,315,018 | A | 2/1982 | Rossignol |
| 5,387,598 | A | 2/1995 | Rossignol |
| 5,578,621 | A | 11/1996 | Rossignol |

(Continued)

FOREIGN PATENT DOCUMENTS

| | | |
|---|---|---|
| EP | 0755386-81 | 6/2002 |
| EP | 0755386 B1 | 6/2002 |

(Continued)

OTHER PUBLICATIONS

"Romark to Develop Alina® (nitazoxanide) as New Treatment for Chronic Hepatits C." Romark Laboratories. Jan. 10, 2006. Web. Aug. 5, 2009. www.natap.orq/2006/HCV/011006 02.htm.
"What is Viral Hepatits?" Centers for Disease Control and Prevention. Apr. 1, 2008. Web. Dec. 14, 2009. www.cdc.aov/hepatitis/PublicInfo.htm.

(Continued)

*Primary Examiner* — Timothy J. Kugel
(74) *Attorney, Agent, or Firm* — Foley & Lardner LLP

(57) ABSTRACT

The present disclosure relates to methods for treating viral hepatitis, compounds useful in the treatment of viral hepatitis, and pharmaceutical compositions comprising such compounds. In one embodiment, pharmaceutical compositions comprising nitazoxanide, tizoxanide, or derivatives and/or mixtures thereof are provided, as well as methods of treating hepatitis C using such compositions.

41 Claims, 10 Drawing Sheets

(56) References Cited

U.S. PATENT DOCUMENTS

| | | | | |
|---|---|---|---|---|
| 5,856,348 | A | 1/1999 | Rossignol | |
| 5,859,038 | A | 1/1999 | Rossignol | |
| 5,886,013 | A | 3/1999 | Rossignol | A61K 31/426 514/367 |
| 5,925,622 | A | 7/1999 | Rossignol et al. | |
| 5,935,591 | A | 8/1999 | Rossignol et al. | |
| 5,965,590 | A | 10/1999 | Rossignol | |
| 5,968,961 | A | 10/1999 | Rossignol | |
| 6,020,353 | A | 2/2000 | Rossignol | |
| 6,117,894 | A | 9/2000 | Rossignol | |
| 6,180,136 | B1 | 1/2001 | Larson et al. | |
| 6,340,696 | B1 | 1/2002 | Camden | |
| 6,423,338 | B1 | 7/2002 | Larson et al. | |
| 6,576,636 | B2 | 6/2003 | Webb et al. | |
| 7,125,568 | B2 | 10/2006 | Sung | |
| 7,645,783 | B2 * | 1/2010 | Rossignol | 514/371 |
| 8,633,230 | B2 * | 1/2014 | Rossignol | 514/370 |
| 9,351,937 | B2 * | 5/2016 | Rossignol | A61K 9/209 |
| 9,827,227 | B2 * | 11/2017 | Rossignol | A61K 31/426 |
| 2001/0002404 | A1 | 5/2001 | Webb et al. | |
| 2004/0081711 | A1 | 4/2004 | Rao et al. | |
| 2005/0129695 | A1 | 6/2005 | Mercken et al. | |
| 2006/0089396 | A1 | 4/2006 | Rossignol | |
| 2006/0194853 | A1 | 8/2006 | Rossignol | |
| 2018/0085353 | A1 * | 3/2018 | Rossignol | A61K 31/426 |

FOREIGN PATENT DOCUMENTS

| | | | |
|---|---|---|---|
| EP | 1213029 | A1 | 6/2002 |
| EP | 1222921 | A1 | 7/2002 |
| EP | 1005342-81 | | 12/2002 |
| EP | 1005342 | B1 | 12/2002 |
| WO | WO-95028393 | A1 | 10/1995 |
| WO | WO-04041295 | A1 | 5/2004 |
| WO | WO-05049065 | A2 | 6/2005 |
| WO | WO-06031566 | A2 | 3/2006 |
| WO | WO-06110814 | A2 | 10/2006 |
| WO | WO-07081974 | A2 | 7/2007 |

OTHER PUBLICATIONS

Stockis et al. "Nitazoxanide Pharmacokinetics and Tolerability in Man After Single Ascending Oral Doses." Int. J. Clin. Pharmacol. Ther. 40.5(2002):213-220.

Stockis et al. "Nitazoxanide Pharmacokinetics and Tolerability in Man During 7 Days of 0.5 g and 1 q b.i.d. Dosing." Int. J. Clin. Pharmacol. Ther. 40.5(2002):221-227.

Fabris et al. "Type 1 Diabetes Mellitus in Patients with Chronic Hepatitis C Before and After Interferon Therapy." *Ailment Pharmacol. Ther.* 18(2003):549-558.

Fung et al. "Viral Hepatitis in 2003." *Curr. Opin. Gastroenterol.* 20.3(2004):241-247.

Ortiz et al. "Randomized Clinical Study of Nitazoxanide Compared to Metronidazole in the Treatment of Symptomatic Giardiasis in Children from Northern Peru." *Ailment Pharmacol. Ther.* 15(2001):1409-1415.

Rossignol et al. "Effect of Nitazoxanide for Treatment of Severe Rotavirus Diarrhea: Randomised Double-Blind Placebo-Controlled Trial." *Lancet.* 368.9530(2006):124-129.

Rossignol et al. "Effect of Nitazoxanide in Persistent Diarrhea and Enteritis Associated With *Blastocystis hominis." Clin. Gastroenterol. Hepatol.* 3(2005):987-991.

Rossignol et al. "Nitazoxanide in the Treatment of Viral Gastroenteritis: A Randomized Double-Blind Placebo-Controlled Clinical Trial." *Ailment Pharmacol. Ther.* 24(2006):1423-1430.

Rossignol et al. "Nitazoxanide in Treating Chronic Hepatitis C: in Vitro Activity and a Clinical Case Report." *Gastroenterol.* 130(2006):A-841. (Abstract #T1821).

Rossignol et al. "Treatment of Diarrhea Caused by *Cryptosporidium parvum:* A Prospective Randomized, Double-Blind, Placebo-Controlled Study of Nitazoxanide." *J. Infect. Dis.* 184(2001):103-106.

Rossignol et al. "Treatment of Diarrhea Caused by *Giardia intestinalis* and *Entamoeba histolytica* or *E. dispar:* A Randomized, Double-Blind, Placebo-Controlled Study of Nitazoxanide." J. Infect. Dis. 184(2004):381-384.

* cited by examiner

VIRAL HEPATITIS TREATMENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a Reissue Application of U.S. Pat. No. 9,107,913, which issued on Aug. 18, 2015 from U.S. application Ser. No. 14/137,280, which is a Continuation of U.S. application Ser. No. 11/651,672, which issued as U.S. Pat. No. 8,633,230, which* claims priority under 35 U.S.C. [§119] *§ 119* to Provisional U.S. Patent Application Ser. No. 60/757,036, filed Jan. 9, 2006, the disclosure of which is incorporated by reference herein.

GOVERNMENT RIGHTS

The U.S. Government has certain rights in this invention pursuant to Contract No. NO1-AI-30046 awarded by the NIAID.

TECHNICAL FIELD

The present disclosure relates to methods for treating viral hepatitis, compounds useful in the treatment of viral hepatitis, and pharmaceutical compositions comprising such compounds.

BACKGROUND

Hepatitis refers to a variety of conditions that involve inflammation of the liver. Viral hepatitis, of which there are several types (e.g., hepatitis A, B, C, D, and E), is an inflammation of the liver due to a viral infection. Each type of viral hepatitis may exhibit different symptoms and may be characterized by different approaches to treatment and prevention. For example, vaccines have been developed for hepatitis A and B, but not for hepatitis C or E.

The main goal of treatment of chronic hepatitis C is to eliminate detectable viral RNA from the blood. Patients lacking detectable hepatitis C virus RNA in the blood 24 weeks after completing therapy typically have a favorable prognosis and may be considered to be cured of the virus. Such a condition is known as a sustained virologic response. For patients not achieving a sustained virologic response, there may be other more subtle benefits of treatment, such as slowing the progression of liver scarring (fibrosis).

Treatment of hepatitis C virus (HCV) commonly involves administration of injectable interferon (or injectable pegylated interferon), ribavirin, or a combination thereof. Interferon alpha is a naturally occurring glycoprotein that is secreted by cells in response to viral infections. It exerts its effects by binding to a membrane receptor. Receptor binding initiates a series of intracellular signaling events that ultimately leads to enhanced expression of certain genes. This leads to the enhancement and induction of certain cellular activities including augmentation of target cell killing by lymphocytes and inhibition of virus replication in infected cells. Ribavirin is a synthetic nucleoside that has activity against a broad spectrum of viruses.

Interferon alpha, with or without ribavirin, is associated with may side effects. Flu-like symptoms, depression, rashes, other unusual reactions and abnormal blood counts are common examples of such side effects. Ribavirin is associated with a significant risk of abnormal fetal development. Accordingly, women who are potentially pregnant should not begin therapy until a report of a negative pregnancy test has been obtained. Female patients are advised to avoid becoming pregnant during treatment. Patients using interferon alpha and ribavirin are advised to have blood tests approximately once a month, and somewhat more frequently at the beginning of treatment. Certain groups of patients cannot take ribavirin, for example those with anemia, heart disease or kidney disease. In such cases, pegylated interferon alpha is typically prescribed alone. Some patients with hepatitis C (e.g., patients also having advanced liver disease) are advised not to take interferon alpha or pegylated interferon alpha because of the risk of serious side effects. For such patients, no previously available method of treatment is recognized as being effective and safe for treating hepatitis C.

There is therefore a need in the art to develop an effective method of treatment of hepatitis C. An ideal method of treatment would achieve a sustained virologic response in a wide range of patients. Such a treatment would employ readily available active agents and would have minimal side effects. When co-administration of interferon alpha is employed, an ideal method of treatment would require reduced amounts of interferon alpha (i.e., reduced frequency of administration, reduced amount per administration, or both) as compared with traditional methods of treatment.

SUMMARY OF THE DISCLOSURE

The present invention is directed at addressing one or more of the abovementioned drawbacks of known methods for treating viral hepatitis C.

In one embodiment, then, the disclosure describes a method of treating a patient suffering from hepatitis C. The method comprises administering to the patient a therapeutically effective amount of a compound selected from nitazoxanide, tizoxanide, derivatives of nitazoxanide, and derivatives of tizoxanide.

In another embodiment, the disclosure describes a method for treating a patient suffering from viral hepatitis. The method comprises administering to the patient a therapeutically effective amount of a first compound having the structure of formula I: R1-NHCO—R2. In formula I, R1 and R2 are independently selected from moieties that provide improved stability of the NHCO group in biological fluid and tissue. In one aspect of the embodiment, the first compound is neither nitazoxanide nor tizoxanide.

In yet another embodiment, the disclosure describes an improvement in a method for treating a patient suffering from hepatitis C comprising administering to the patient a therapeutically effective amount of nitazoxanide, tizoxanide, or mixtures thereof.

In yet another embodiment, the disclosure describes a method of treating a patient suffering from hepatitis C. The method comprises pretreating the patient by administering to the patient for a predetermined period of time a first composition comprising a therapeutically effective amount of a compound selected from nitazoxanide, tizoxanide, derivatives of nitazoxanide, and derivatives of tizoxanide, or mixtures thereof. The method further comprises administering to the patient, after the predetermined period of time, a therapeutically effective amount of a second composition comprising an active agent.

In yet another embodiment, the disclosure describes a composition comprising: (a) one or more compounds selected from nitazoxanide, tizoxanide, derivatives of nitazoxanide, and derivatives of tizoxanide; (b) an interferon; and (c) an anti-diabetes agent.

In yet another embodiment, the disclosure describes compositions effective in the methods of treatment disclosed herein.

DETAILED DESCRIPTION OF THE INVENTION

Definitions and Nomenclature

Figure 1A:
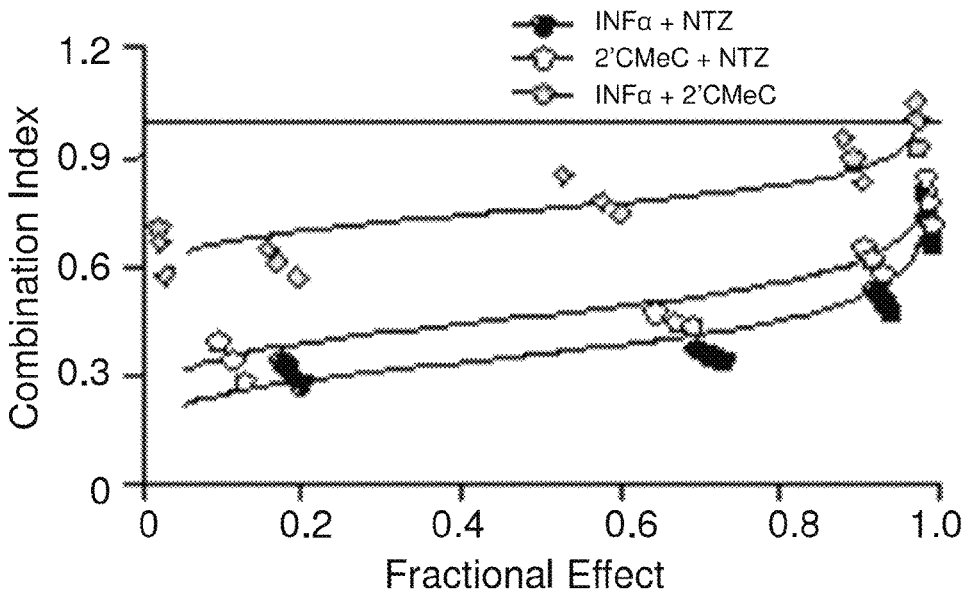
FIGS. 1a and 1b are graphs illustrating the synergistic activity of nitazoxanide with interferon alpha-2b or 2'-C-methyl cytidine against HCV replication in an HCV replicon containing cell line.

Before describing the present invention in detail, it is to be understood that unless otherwise indicated, this invention is not limited to particular dosages, formulations or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a dosage form" refers not only to a single dosage form but also to a combination of two or more different dosage forms, "an active agent" refers to a combination of active agents as well as to a single active agent, and the like.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The terms "treating" and "treatment" as used herein refer to reduction in severity and/or frequency of symptoms, elimination of symptoms and/or underlying cause, prevention of the occurrence of symptoms and/or their underlying cause (e.g., prophylactic therapy), improvement or remediation of damage, or reduction in intensity of infection.

By the terms "effective amount" and "therapeutically effective amount" of a compound of the invention is meant a nontoxic but sufficient amount of the drug or agent to provide the desired effect.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

By "patient," or "subject" is meant any animal for which treatment is desirable. Patients may be mammals, and typically, as used herein, a patient is a human individual.

The present disclosure includes compounds of formula I: R1-NHCO—R2, as well as their use in the treatment of hepatitis, particularly hepatitis C, and pharmaceutical compositions comprising them.

In one embodiment of formula I, R1 and R2 are independently selected from moieties that stabilize (i.e., provide improved stability of) the NHCO group. By "stabilize" is meant that the NHCO group is less prone to reaction in biological fluid and tissue as compared with an unsubstituted NHCO group (e.g., $NH_2COH$, R1-NHCOH, $NH_2CO$—R2, and the like), that is, as compared with the analogous compound having hydrogen as either R1 or R2. Such reactions include cleavage of the NHCO group (e.g., breakage of the nitrogen-carbon bond), addition to the NHCO group, substitution reactions, hydrogenation reactions, hydration reactions, oxidation reactions, reduction reactions, and the like.

In one embodiment, the compounds of formula I exclude nitazoxanide and tizoxanide. In another embodiment, the compounds of formula I include nitazoxanide and tizaxanide.

In another embodiment, R1 and R2 are each a substituted or unsubstituted cyclic group. Such groups may be heterocyclic groups or a carbocyclic group such as an aryl or cycloalkyl group. In one example, R1 is a heterocyclic ring and R2 is an aryl, optionally substituted by one to three substituents. Another example group of compounds of formula I includes compounds wherein R1 and R2 are both benzene, each optionally substituted by one to three substituents.

In yet another embodiment, R1 is selected from thiazole and thiadiazole substituted by one to three substituents, and R2 is benzene substituted by one to three substituents.

Examples of substituents for R1 and R2 include OH, alkoxy, halo, alkyl, fluoroalkyl, ester, thioalkyl, and functional groups. Specific examples include fluoro, bromo, OAc, $CH_3$, $CF_3$, $NO_2$, $CH_2CO_2Et$, $SCH_3$, $OCH_3$ and the like.

Examples of the heterocyclic groups for R1 and R2 include aromatic heterocyclic groups or saturated or unsaturated non-aromatic heterocyclic groups (alicyclic heterocyclic group). Such groups contain, besides carbon atoms, at least one heteroatom (preferably 1 to 4 heteroatom(s), more preferably, 1 to 2 heteroatom(s)), and may contain from 1 to 3 different kind of heteroatoms, (preferably 1 to 2 kinds of heteroatom(s)). As used herein, the term "heteroatom" is meant to include oxygen atoms, sulfur atoms, and nitrogen atoms.

Examples of the "aromatic heterocyclic group" include an aromatic monocyclic heterocyclic group such as a 5 or 6-membered aromatic monoyclic heterocyclic group (e.g., furyl, thienyl, pyrrolyl, oxazolyl, isooxazolyl, thiazolyl, thiadiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as a 8 to 12-membered aromatic fused heterocyclic group (e.g., benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, alpha-carbolinyl, beta-carbolinyl, gamma-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridaizinyl); preferably, a heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group.

Examples of the "non-aromatic heterocyclic group" include a 3 to 8-membered (preferably 5 or 6-membered) saturated or unsaturated (preferably saturated) non-aromatic heterocyclic group (aliphatic heterocyclic group) such as oxiranyl, azetidinyl, oxetanyl, thiethanyl, pyrrolidinyl, tetrahydrofuryl, thiolanyl, piperidinyl, tetrahydropyranyl, morpholinyl, thiomorpholinyl, piperazinyl.

In one embodiment of compounds having the structure of formula I, R1 is heterocyclic. In another embodiment, R1 is heterocyclic comprising 2 or 3 heteroatoms. In yet another embodiment, R1 is substituted heterocyclic and comprises 2 or 3 heteroatoms. In yet another embodiment, R1 is heterocyclic, substituted with 1, 2, or 3 groups selected from hydroxide, halogen (i.e., iodo, chloro, bromo, or fluoro), alkoxy (e.g., $OCH_3$), fluoroalkyl (e.g., $CF_3$), ester (e.g., $CH_2CO_2Et$), thioalkyl (e.g., $SCH_3$), OAc, and alkyl (e.g., $CH_3$). For example, R1 is thiazole or substituted thiazole.

In one embodiment of compounds having the structure of formula I, R2 is aryl. In another embodiment, R2 is substituted aryl. In yet another embodiment, R2 is aryl that comprises 2, 3, or 4 substituents. In another embodiment, R2 is aryl and comprises substituents in the ortho and meta positions (relative to the point of attachment of the aryl group to the carbonyl group of formula I). In still another embodiment, R2 is aryl comprising 2 or more substituents selected from hydroxide, halogen (i.e., iodo, chloro, bromo, or fluoro), alkoxy (e.g., $OCH_3$), fluoroalkyl (e.g., $CF_3$), ester (e.g., $CH_2CO_2Et$), thioalkyl (e.g., $SCH_3$), OAc, and alkyl (e.g., $CH_3$).

In one embodiment of the compounds having the structure of formula I, the reactivity of the NHCO group in the compound is reduced toward cleavage reactions compared with the reactivity of the analogous compound having hydrogen as either R1 or R2.

In another embodiment, R1 and R2 are independently selected from substituted cyclic groups, unsubstituted cyclic groups, substituted heterocyclic groups, and unsubstituted heterocyclic groups, wherein either R1, R2, or both R1 and R2 are optionally aromatic. In yet another embodiment, R1 and R2 are selected from aryl, substituted aryl, heteroaryl, substituted heteroaryl, alicyclic, substituted alicyclic, heterocyclic, and substituted heterocyclic. In yet another embodiment, R1 and R2 are each substituted with from one to three substituents independently selected from OH, $NO_2$, alkoxy (such as methoxy), halo (such as F and Br), alkyl (such as methyl), fluoroalkyl (such as fluoromethyl), ester (such as OAc, and $CH_2CO_2Et$), and thioalkyl (such as thiomethyl). In a still further embodiment, at least one of R1 and R2 is heterocyclic. In a still further embodiment, at least one of R1 and R2 comprises between 1 and 3 heteroatoms. In yet another embodiment, at least one of R1 and R2 comprises a heterocyclic group selected from aromatic monocyclic heterocycles, aromatic fused heterocycles, and non-aromatic heterocycles. In a still further embodiment, at least one of R1 and R2 comprises a heterocyclic group selected from furyl, thienyl, pyrrolyl, oxazolyl, isooxazolyl, thiazolyl, thiadiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, alpha-carbolinyl, beta-carbolinyl, gamma-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridaizinyl), oxiranyl, azetidinyl, oxetanyl, thiethanyl, pyrrolidinyl, tetrahydrofuryl, thiolanyl, piperidinyl, tetrahydropyranyl, morpholinyl, thiomorpholinyl, and piperazinyl, any of which may be optionally substituted with 1 to 3 substituents. In another embodiment, R1 is a heterocyclic group optionally substituted with 1 to 3 substituents and R2 is aryl optionally substituted with 1 to 3 substituents. In yet another embodiment, R1 is thiazole or thiadiazole optionally substituted with 1 to 3 substituents. In a still further embodiment, R2 is phenyl optionally substituted with 1 to 3 substituents. In a still further embodiment, R1 and R2 are both aryl, each optionally substituted with 1 to 3 substituents.

Examples of compounds that have the structure of formula I include nitazoxanide, tizoxanide, RM-4803, RM-4819, RM-4832, and RM-4850, wherein nitazoxanide, tizoxanide, RM-4819, RM-4832, and RM-4850 are particularly preferred. The structures of these compounds are shown in the following list:

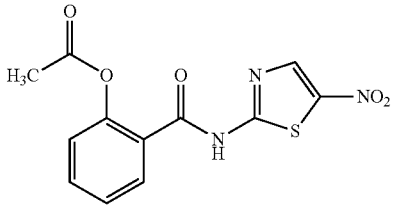

Nitazoxanide

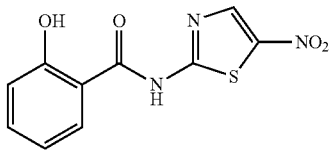

Tizoxanide

RM-4803

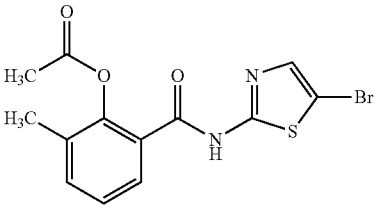

RM-4819

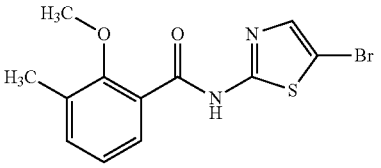

RM-4832

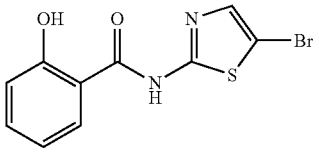

RM-4850

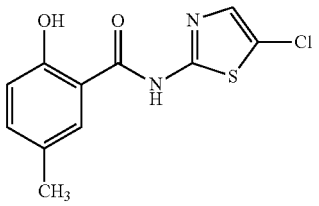

As described below, the compositions of the current disclosure comprise, as an active agent, compounds having the structure of formula I in a pharmaceutically acceptable form. If desired, the compositions may further comprise one or more additional active agents (also described in detail below). Where it is appropriate, any of the active agents may be administered in the form of the compound per se, and/or in the form of a salt, polymorph, ester, amide, prodrug, derivative, or the like, provided the salt, polymorph, ester, amide, pro-drug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

Compounds having the structure of formula I may be prepared according to literature methods. For example, the preparation of compounds 1a and 1b are described in U.S. Pat. No. 3,950,351, and WO 95/28393, respectively. Synthetic methods for the preparation of analogues and derivatives of 1a and 1b, as well as other compounds having structures that fall within the scope of formula I, employ known procedures that will be apparent to the skilled artisan.

Pharmaceutical compositions according to this disclosure comprise a compound having the structure of formula I, as described herein. Such pharmaceutical compositions may also comprise: (1) one or more additional compounds having the structure of formula (I); (2) one or more pharmaceutically acceptable carriers as disclosed herein; and (3) one or more additional components as described herein. The compositions may contain from 0.05% to 95% by weight of the active agent(s), with the pharmaceutically acceptable carrier(s) and any additional components forming the 5% to 99.95% by weight that remains.

One or more additional active agents may be included in the pharmaceutical compositions and methods of treatment described herein. In one embodiment, the additional active agent is effective in treating hepatitis. For example, the compositions may include one or more additional therapeutic agents useful in treating hepatitis C such as ribavirin and immune-stimulating agents such as interferons, including interferon α-2b, a derivative of interferon α-2b such as a polyethylene glycol-conjugated form of interferon α-2b, interferon α-2a, or interferon alfacon-1. Specific examples also include Omega IFN (BioMedicines Inc., Emeryville, Calif.); BILN-2061 (Boehringer Ingelheim Pharma KG, Ingelheim, Germany); Summetrel (Endo Pharmaceuticals Holdings Inc., Chadds Ford, Pa.); Roferon A, Pegasys, Pegasys and Ribavirin, and CellCept (F. Hoffmann-La Roche LTD, Basel, Switzerland); Wellferon (GlaxoSmithKline plc, Uxbridge, UK) Albuferon-α (Human Genome Sciences Inc., Rockville, Md.); Levovirin (ICN Pharmaceuticals, Costa Mesa, Calif.); IDN-6556 (Idun Pharmaceuticals Inc., San Diego, Calif.); IP-501 (Indevus Pharmaceuticals Inc., Lexington, Mass.); Actimmune (InterMune Inc., Brisbane, Calif.); Infergen A (InterMune Pharmaceuticals Inc., Brisbane, Calif.); ISIS 14803 (ISIS Pharmaceuticals Inc, Carlsbad, Calif./Elan Phamaceuticals Inc., New York, N.Y.); JTK-003 (Japan Tobacco Inc., Tokyo, Japan); Ceplene, Pegasys and Ceplene (Maxim Pharmaceuticals Inc., San Diego, Calif.); Civacir (Biopharmaceuticals Inc., Boca Raton, Fla.); Intron A and Zadaxin (RegeneRx Biopharmiceuticals Inc., Bethesda, Md./SciClone Pharmaceuticals Inc, San Mateo, Calif.); Levovirin, Viramidine (Ribapharm Inc., Costa Mesa, Calif.); Heptazyme (Ribozyme Pharmaceuticals Inc., Boulder, Colo.); Intron A, PEG-Intron, Rebetron, Ribavirin, PEG-Intron/Ribavirin (Schering-Plough Corporation, Kenilworth, N.J.); Zadazim (SciClone Pharmaceuticals Inc., San Mateo, Calif.); Rebif (Serono, Geneva, Switzerland); IFN-β and EMZ701 (Transition Therapeutics Inc., Ontario, Canada); T67 (Tularik Inc., South San Francisco, Calif.); VX-497 (Vertex Pharmaceuticals Inc., Cambridge, Mass.); VX-950/LY-570310 (Vertex Pharmaceuticals Inc., Cambridge, Mass./Eli Lilly and Co. Inc., Indianapolis, Ind.); Omniferon (Viragen Inc., Plantation, Fla.); and XTL-002 (Biopharmaceuticals Ltd., Rehovot, Isreal).

In addition to or instead of anti-hepatitis agents, pharmaceutical compositions and methods described herein may comprise one or more additional active agent as appropriate. Additional active agents include those effective in treating disorders of the endocrine system such as diabetes and hyper-insulinemia. Examples of anti-diabetes agents include insulin, pramlintide, exenatide, sulfonylureas (e.g., chlorpropamide, glipizide, glyburide, glimepiride), meglitinides (e.g., repaglinide, nateglinide), biguanides (e.g., metformin), thiazolidinediones (e.g., rosiglitazone, troglitazone, pioglitazone), and α-glucosidase inhibitors (e.g., acarbose, meglitol). Such active agents may be administered either prior to or concurrently with administration of the compounds disclosed herein in order to regulate plasma levels of insulin. When administered concurrently, such additional active agents may be administered as part of the same formulation with the compounds disclosed herein, or they may be administered in a separate formulation. Similarly, other active agents such as those effective in treating diseases of the liver may also be used with the compounds disclosed herein.

Pharmaceutical compositions comprising the compounds of the disclosure that are suitable for the uses described herein may also comprise a pharmaceutically acceptable carrier. Appropriate pharmaceutical carriers may depend, for example, on the method of administration of the compositions, as will be appreciated by one of skill in the art.

Pharmaceutically acceptable carriers may be solid or liquid, or mixtures thereof. Pharmaceutically acceptable carriers are materials such as binders, lubricants, disintegrants, fillers, surfactants, emulsifiers, coloring agents, and the like. Binders are used to impart cohesive qualities, and thus ensure that the composition remains intact (e.g., as an implant or tablet). Suitable binder materials include, but are not limited to, polymer matrices, hydrogels, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate manufacture, promoting powder flow and preventing particle capping (i.e., particle breakage) when pressure is relieved. Useful lubricants are magnesium stearate, calcium stearate, and stearic acid. Disintegrants are used to facilitate disintegration of the composition, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Surfactants are wetting agents, and may include ionic materials such as fatty acid salts and non-ionic materials such as PLURONICS™ (such as F-127, L-122, L-101, L-92, L-81, and L-61).

For example, the pharmaceutically acceptable carrier for the compositions disclosed herein may comprise one or more biocompatible polymer. By "biocompatible" is meant a material that does not illicit an adverse response when subjected to a biological environment such as by implantation or injection in vivo. Furthermore, in one embodiment, biocompatible materials do not illicit an immune response when administered in vivo. Unless otherwise stated, biocompatible materials include materials that are bioerodible, biodegradable and bioresorbable.

Polymer carriers such as biocompatible polymers may be homopolymers or copolymers of any of the monomer units described herein. Furthermore, copolymers are not limited to any specific architecture, and may consist of random, alternating, block (including multiblock), star, comb, graft, and dendrimer-type copolymers, as well as combinations thereof. Blends of more than one bioerodible polymer are also within the scope of this disclosure. It will be appreciated that crosslinked and crosslinkable polymers may be used as long as such crosslinking does not adversely affect the material's ability to form the compositions described herein (e.g., the material's ability to bioerode). For example, reversible crosslinks (wherein the crosslinks comprise non-covalent and/or weakly covalent intermolecular bonds) may be present prior to administration of the compositions, or such bonds may form in vivo.

Suitable bioerodible polymers may comprisepoly(orthoester)s, poly(lactone)s such as poly(ε-caprolactone) and poly (γ-caprolactone), poly(lactide)s, poly(lactic acid), poly(glycolide)s, poly(glycolic acid), poly(ethylene terephthalate), poly(butyric acid), poly(valeric acid), polymers of anhydrides, poly(vinyl alcohol), poly(ethylene vinyl acetate), polymers of α-hydroxycarboxylic acid and derivatives thereof, albumin, collagen, gelatin, hyaluronic acid, starch, cellulose and cellulose derivatives (e.g., methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly (ether ester) multiblock copolymers, poly(ether)s such as poly(ethylene glycol), and poly(butylene terephthalate), tyrosine-derived polycarbonates, poly(hydroxyl acids), poly (hydroxybutyrate), polydioxanone, poly(alkylcarbonate), poly(hydroxyvaleric acid), polydioxanone, degradable polyesters, poly(malic acid), poly(tartronic acid), poly(acrylamides), polyphosphazenes, poly(amino acids), poly(alkylene oxide)-poly(ester) block copolymers, poly(hydroxybutyric acid), poly(beta-butyrolactone), poly(gamma-butyrolactone), poly(gamma-valerolactone), poly(d-decanolactone), poly(trimethylene carbonate), poly(1,4-dioxane-2-one) or poly(1,5-dioxepan-2-one), or combinations thereof (i.e., copolymers of the constituent monomer units, blends, etc.).

Examples of biodegradable polymers include synthetic polymers such as polymers of lactic acid and glycolic acid, polyanhydrides, poly(ortho)esters, polyurethanes, poly(butyric acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion The components of a composition may be distributed homogeneously throughout the pharmaceutically acceptable carrier, or localized regions of concentration gradients may exist. By "homogeneous distribution" is meant to included instances of molecular homogeneity as well as bulk or macroscopic homogeneity. For example, the active agent may be homogeneously distributed on a molecular level (as for a solute homogeneously distributed within a solvent) or on a macroscopic level (as for discrete particles of active agent homogeneously distributed throughout the carrier). Components of a composition may be attached (covalently or otherwise, including physisorbed, ionically associated, and the like) to the pharmaceutically acceptable carrier.

For compositions administered as aqueous or other solvent-based dosage forms (e.g., for parenteral administration), a variety of liquid carriers may be used. Aqueous solutions may include salts, buffers, and the like. Non aqueous liquid carriers include, for example, fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like In addition to one or more pharmaceutically acceptable carrier, pharmaceutical compositions comprising one or more of the compounds disclosed herein and suitable for the uses described herein may also comprise one or more additional components. Additional components include, for example, salts, buffers, penetration enhancers, absorption accelerants, gel forming materials such as polymers, visualization aids, dispersing agents, stabilizers, excipients, and plasticizers.

Buffers are compounds or solutions that are employed to aid in maintaining the concentration of an analyte within a desired range. For example, pharmaceutically acceptable pH buffers are used to maintain the acidity or basicity of a solution within a pharmaceutically acceptable range. Buffers for use in the compositions disclosed herein may be any known or hereafter discovered buffer.

Penetration enhancers include compounds that enable or enhance permeation of compositions across boundaries such as membranes. Examples of penetration enhancers may be found in the relevant literature (e.g., Percutaneous Penetration Enhancers, Smith and Maibach, eds., CRC Press, New York N.Y., 2005) and include cyclohexanone derivatives, cyclic monoterpenes, pyrrolidones, dioxolanes, 1-dodecylazacycloheptan-2-one (Azone), dimethylsulfoxide (DMSO), and limonene.

Gel forming materials may be polymers or non-polymers, and are generally able to form a gelatinous network. In one embodiment, gel forming materials are able to form gels in vivo, whereas in other embodiments, gel formation takes place ex vivo. Examples of gel forming materials include collagen, chitosan, pectins, hyaluronic acid, and the like.

Dispersing agents are surfactants (for example, as described herein) in combination with a solvent such as water.

Plasticizers are compounds used to plasticize (i.e., soften) plastic and other materials. Examples include propylene glycol, acetyl tributyl citrate, acetyl triethyl citrate, p-tert-butylphenyl salicylate, butyl stearate, butylphthalyl butyl glycolate, dibutyl sebacate, di-(2-ethylhexyl)phthalate, diethyl phthalate, diisobutyl adipate, diisooctyl phthalate, diphenyl-2-ethylhexyl phosphate, epoxidized soybean oil, ethylphthalyl ethyl glycolate, glycerol monooleate, monoisopropyl citrate, mono, di-, and tristearyl citrate, triacetin (glycerol triacetate), triethyl citrate, and 3-(2-Xenolyl)-1,2-epoxypropane.

Excipients are inactive ingredients that may be employed in the compositions described herein for a variety of reasons. A wide range of excipients are described in the literature (e.g., Rowe et al., Handbook of Pharmaceutical Excipients, McGraw Hill, 2006).

Visualization aids are compounds that aid visualization of the drug delivery composition or any of the components thereof via a visualization method such as fluoroscopy, magnetic resonance imaging (MRI), visible light, ultrasound, or radiography. Any visualization aids known in the art may be used in the compositions disclosed herein.

In one aspect, the compositions of the present disclosure include one or more preservatives or bacteriostatic agents, present in an effective amount to preserve the composition and/or inhibit bacterial growth in the composition. Examples include bismuth tribromophenate, methyl hydroxybenzoate, bacitracin, ethyl hydroxybenzoate, propyl hydroxybenzoate, erythromycin, 5-fluorouracil, methotrexate, doxorubicin, mitoxantrone, rifamycin, chlorocresol, benzalkonium chlorides, paraoxybenzoic acid esters, chlorobutanol, benzylalcohol, phenethyl alcohol, dehydroacetic acid, sorbic acid, and the like.

Stabilizers include compounds such as antioxidants, and are used to inhibit or retard decomposition reactions that include, by way of example, oxidative reactions. Examples of stabilizer include butylated hydroxytoluene (BHT), butylated hydroxyanisole (BHA), ascorbic acid, ethylene diamine tetraacetic acid (EDTA), tocopherol-derived compounds such as alpha-tocopherol, sulfites, tert-butylhydroquinone, citric acid, acetic acid, and pectin.

The compositions disclosed herein or the precursors thereof may further contain porosifying agents that achieve greater surface area of, for example, an implant or tablet. Examples of porosifying agents include inorganic salts, sucrose, surfactants, small molecular weight polymers, fast degrading polymers, thermoreversible polymer precipitates, gas bubbles, and cavitation bubbles.

The amount of active agent (as well as other active ingredients, when present) in the compositions disclosed herein will depend on a number of factors and will vary from subject to subject. Such factors will be apparent to one of ordinary skill in the art, and may include the particular disorder or condition being treated, the mode of administration, the severity of the symptoms, the patient's age, weight and general condition, and the judgment of the prescribing physician.

In one embodiment, a composition comprises a compound of formula I as an active agent and a pharmaceutically acceptable carrier. The carrier may be used in any convenient amount relative to the active agent, and the weight ratio of the carrier to active agent can vary from about 0.1 to 1 to about 100,000 to 1 depending upon the application. In one example of this embodiment, the composition consists only of the active agent and a pharmaceutically acceptable carrier. In another example, the composition comprises the active agent, a carrier, and one or more additional components such as those described herein. In a still further example, the composition comprises the active agent, a second active agent, one or more carriers, and one or more additional components.

Compounds having the structure of formula I as disclosed herein are useful as medicaments and as active agents in pharmaceutical compositions. In one embodiment, such compounds and compositions are useful in the treatment of viral hepatitis. In particular, the compounds and compositions are useful in the treatment of patients suffering from hepatitis B virus (HBV) and hepatitis C virus (HCV).

In another embodiment, the compounds described herein are useful in an improved method of treating hepatitis C with an interferon, wherein the improvement comprises administering an effective amount of nitazoxanide, tizoxanide, or mixtures thereof to a subject in need thereof. By way of this improvement, the percentage of subjects exhibiting reduced serum HCV RNA is increased in comparison to a method of treating hepatitis C with the interferon or with a combination of ribavirin and the interferon. In addition, the amount of interferon required to achieve a sustained virologic response in the patient may be reduced compared to the amount of interferon required to achieve a sustained virologic response in the patient without administration of nitazoxanide, tizoxanide, or mixtures thereof. Furthermore, the amount of interferon required to achieve a sustained virologic response in the patient may be reduced compared to the amount of interferon required to achieve a sustained virologic response in the patient when treated with a combination of ribavirin and the interferon. In one embodiment, a method of treatment is provided wherein a patient suffering from hepatitis C is pre-treated using nitazoxanide and/or tizoxanide prior to being treated with an interferon (such as any of the interferons described herein). Specific examples of this and other embodiments are described in more detail hereinbelow.

Nitazoxanide, tizoxanide, and mixtures thereof are particularly effective in the treatment of hepatitis C. By treating hepatitis C patients with nitazoxanide, tizoxanide, or a mixture thereof, it may be possible to reduce the amount of interferon needed for effective treatment, although such reduction is not necessary. It may also be possible to avoid the use of ribavirin completely, although this too is not necessary. These benefits may be obtained while simultaneously increasing the percentage of subjects who respond favorably in terms of a reduction of serum HCV RNA. Thus, the present disclosure describes a method of treating hepatitis C comprising administering to a subject in need thereof an effective amount of nitazoxanide, tizoxanide, or a mixture thereof. Similarly, the present invention includes any of the foregoing embodiments in which any compound of formula I or combination of such compounds is used in place of nitazoxanide and tizoxanide.

Administration of the compositions described herein may be carried out using any appropriate mode of administration and dosage form. Thus, administration can be, for example, oral, ocular, buccal, rectal, topical, parenteral, transdermal, transmucosal, sublingual, by inhalation (using either solid or liquid compositions), or via an implanted reservoir in a dosage form. It will be appreciated that the most suitable route in any given case will depend on the nature and severity of the condition being treated and on the nature of the particular form of compound of formula I which is being used. The term "parenteral" as used herein is intended to include, for example, subcutaneous, intravenous, intradermal, and intramuscular injection. The term "transmuco sal" as used herein is intended to include, for example, rectal, vaginal, buccal, sublingual, and penile administration. The term "inhalation" as used herein is intended to include inhalation via the nose or the mouth, and includes instances wherein absorption of the composition occurs in the lungs as well as, for example, the mucosal membranes of the mouth, nose, and throat. Administration via implants is meant to include implants affixed anywhere on or positioned anywhere inside the body, including within body cavities (e.g., intraperitoneal implants, intraocular implants, implants in joints, etc.), within organs, and subcutaneously.

Depending on the intended mode of administration, the pharmaceutical composition may be a solid, semi-solid, or liquid such as, for example, a tablet, a capsule, a caplet, an aerosol, a liquid, a suspension, an emulsion, a cream, a gel, a suppository, granules, pellets, beads, a film, a powder, a sponge, or the like.

In one embodiment, the composition comprises a unit dosage form suitable for single administration of a precise dosage. In another embodiment, the composition comprises a reservoir such as in an implant capable of controlled delivery of the composition over time.

Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995). A description of some, but not all, of the suitable dosage forms is provided infra.

Formulations suitable for oral administration may be presented as discrete units, such as capsules, cachets, lozenges, or tablets, each containing a predetermined amount of a compound of formula I; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients).

Tablets may be manufactured using standard tablet processing procedures and equipment. In addition to reversine, tablets will generally contain inactive, pharmaceutically acceptable carrier materials as described herein. Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals. Oral dosage forms, whether tablets, capsules, caplets, or particulates, may, if desired, be formulated so as to provide for gradual, sustained release of the active agent over an extended time period. For example, as will be appreciated by those of ordinary skill in the art, dosage forms may be formulated by dispersing the active agent within a matrix of a gradually hydrolyzable material such as a hydrophilic polymer, or by coating a solid, drug-containing dosage form with such a material.

One example of a preferred dosage form is Alinia® (see Alinia® package insert and/or U.S. Pat. Nos. 5,387,598, 5,578,621, 5,968,961, 5,856,348, 5,859,138, 5,886,013, 5,965,590, 6,020,353, and 6,117,894). It is to be understood that, unless otherwise specified, in the present disclosure (including the examples and claims) any references made to Alinia® are providing only as examples, and are not meant to be limiting. Thus, such references are intended to apply equally to other formulations comprising nitazoxanide, tizoxanide, and/or compounds having the structure of formula I.

Formulations suitable for buccal (e.g., sub-lingual) administration include lozenges comprising a compound of formula I, in a flavored base, usually sucrose and acacia or tragacanth; and pastilles comprising the compound in an inert base such as gelatin and glycerin or sucrose and acacia.

Preparations according to this disclosure suitable for parenteral administration include sterile aqueous and non-aqueous solutions, suspensions, and emulsions. Such preparations are preferably isotonic with the blood of the intended recipient. Injectable aqueous solutions may contain the active agent in water-soluble form, or may contain a suspension or emulsion of the active agent. Examples of nonaqueous solvents or vehicles are described herein. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable compositions may be rendered sterile via, for example, incorporation of a sterilizing agent, filtration through a bacteria-retaining filter, irradiation, or heat. They can also be manufactured using a sterile injectable medium. Any active agents present in the compositions may also be in dried, e.g., lyophilized, form that may be rehydrated with a suitable vehicle immediately prior to administration via injection. Parenteral preparations are preferably administered intravenously, although administration may also be effected by means of subcutaneous, intramuscular, or intradermal injection. In one embodiment, such preparations are prepared by admixing the compound with water or a glycine buffer and rendering the resulting solution sterile and isotonic with the blood.

The compositions disclosed herein may also be administered through the skin using conventional transdermal drug delivery systems, wherein the active agent is contained within a laminated structure that serves as a drug delivery device to be affixed to the skin. In such a structure, the active agent composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the active agent-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer. Formulations for transdermal administration may also be delivered by iontophoresis (see, for example, Pharmaceutical Research 3(6), 318, (1986)) and suitable formulations typically take the form of an optionally buffered aqueous solution of a Compound of formula I. Suitable formulations comprise, for example, citrate or bis/tris buffer (pH 6) or ethanol/water and contain from 0.1 to 0.2M active ingredient.

The compositions disclosed herein may also be administered topically using conventional topical dosage forms, wherein the active agent is contained within a carrier. Dosage forms suitable for topical application include, by way of example, creams, pastes, jellies, gels, ointments, liquids, aerosols, oils, lotions, foams, suspensions, and emulsions. Carriers which may be used include vaseline, lanoline, polyethylene glycols, alcohols, and combinations of two or more thereof.

In addition to the formulations described previously, the compounds may also be formulated as a depot preparation for controlled release of the active agent, preferably sustained release over an extended time period. These sustained release dosage forms may be administered by implantation (e.g., subcutaneously, intraperitoneal, intramuscularly or by intramuscular injection).

Formulations suitable for rectal administration are preferably presented as unit dose suppositories. These may be prepared by admixing a Compound of formula I with one or more conventional solid carriers, for example, cocoa butter, and then shaping the resulting mixture.

Although the compositions disclosed herein will generally be administered orally, parenterally, transdermally, or via an implanted depot, other modes of administration are suitable as well. For example, administration may be rectal or vaginal, preferably using a suppository that contains, in addition to an active agent, excipients such as a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

It will be appreciated that the compositions disclosed herein may be prepared and packaged as single dosage units, such as for oral administration (e.g., tablets). The formulations may also be prepared and packaged as multiple dose formulations, or as dosages suitable for long-term administration, such as for topical administration (e.g., creams), transmembrane administration (e.g., patches), or implantation.

The compounds disclosed herein may be administered for any length of time suitable for the intended use. Administration of the compounds disclosed herein will typically be carried out over a period of about 3 days to about 104 weeks, but may be carried out over a period longer than 104 weeks and may even be carried out indefinitely. For example, treatment of hepatitis C using the compounds disclosed herein will typically involve administration of the compounds over a period of 12, 24, or 48 weeks.

Any appropriate dosage and regimen may be used for the compounds disclosed herein and the pharmaceutical compositions comprising such compounds. In one embodiment, a compound having the structure of formula I is administered in conjunction with an additional active agent such as, for example, an interferon such as any of the interferons described herein. The compound having the structure of formula I and the additional active agent (e.g., an interferon) may be administered as part of the same composition, or they may be administered in separate compositions (including in separate compositions that vary in dosage form, release profiles, and the like).

In one embodiment, a patient suffering from hepatitis C is first pretreated with nitazoxanide, tizoxanide, or any of the compounds disclosed herein having the structure of formula I. The duration of the pretreatment period may be between about 3 days and about 6 months, for example between about 1 week and about 12 weeks, and as a further example between about 1 week and about 4 weeks. The pretreatment period is followed subsequently by a treatment period wherein the pretreated patient is treated with either an interferon alone or an interferon plus nitazoxanide, tizoxanide, or any of the compounds having the structure of formula I. Any of the interferons described herein may be used during the treatment period. The duration of the treatment period will be any duration that is required to obtain the desired response, and will typically be between about 1 day and about 12 months or longer. For example, the treatment period may comprise weekly injections of an interferon, and may involve a single week of treatment, 2-4 weeks of treatment, 4-12 weeks of treatment, or more (such as 6 months, 1 year, 2 years, or indefinitely).

Examples of regimens that are suitable for administration of the compounds disclosed herein include the following: 24 weeks of administration of nitazoxanide followed by 12 weeks of administration of a composition comprising nitazoxanide and interferon α-2b or pegylated interferon α-2b;

2-4 weeks of administration of nitazoxanide followed by 12 weeks of administration of a composition comprising nitazoxanide and pegylated interferon α-2b; administration of a composition comprising nitazoxanide+pegylated interferon α-2b for 12, 24, or 48 weeks; and 12, 24, or 48 weeks of administration of nitazoxanide, tizoxanide, or combinations thereof. It will be appreciated that such regimens are provided only as examples, as suitable durations, dosages, and orders of administration will vary. Appropriate regimens will typically be determined by a physician.

It will be appreciated that dosages may vary, and will typically be selected to provide a therapeutically effective amount of the active agent to the patient. In one example, a dosage may be in the range of about 100 mg to about 2000 mg, or in the range of about 250 mg to about 1000 mg, or preferably about 500 mg. In another specific example, an appropriate dosage is chosen to achieve and maintain a blood level of active agent (e.g., nitazoxanide) in the patient that is between about 0.1 μg/ml and about 10 μg/ml, preferably about 1 μg/ml.

Methods of preparation for the compositions disclosed herein will be apparent to one of ordinary skill. In one embodiment, the formulations of the disclosure may be prepared by uniformly and intimately admixing the active compound with a liquid or finely divided solid carrier, or both, and then, if necessary, shaping the resulting mixture. For example, a tablet may be prepared by compressing or molding a coated or uncoated powder or coated or uncoated granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The present disclosure also provides kits for accomplishing such treatment as described herein. The kits comprise: (i) an effective amount of a compound of formula I; (ii) one or more pharmaceutically acceptable carriers and/or additives; and (iii) instructions for use (e.g., in treating hepatitis).

As used herein, the phrase "instructions for use" shall mean any FDA-mandated labelling, instructions, or package inserts that relate to the administration of a compound of Formula I for the purpose of treating viral hepatitis. For example, instructions for use may include, but are not limited to, indications for the particular disease, identification of specific symptoms of the specific disease that can be ameliorated by the claimed compounds, and recommended dosage amounts for subjects suffering from the disease. The kit of the present invention further comprises a unit dosage amount of the compound effective for treating viral hepatitis.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

EXAMPLES

Example 1

Activity Against HCV Replication

Antiviral activity of nitazoxanide, tizoxanide, interferon α, ribavirin and 2'-C-methyl cytidine was assessed in five different HCV replicon cell lines: (1) AVA5, a subgenomic construct of genotype 1b (Blight et al., 2000, Science 290:1972-1974); (2) H/FL-Neo, a genotype 1a full length construct (Blight et al., 2003, Journal of Virology 77:3181-3190); (3) JWT, a subgenomic construct of genotype 1b (Pfeiffer and Kirkegaard, 2005, Journal of Virology, 79:2346-2355); (4) 4-3-10, a subgenomic construct of genotype 1b, developed by a protocol that involved serial passage of JWT cells in 100 μM for one month followed by 400 μM ribavirin for two weeks (Pfeiffer and Kirkegaard, 2005, Journal of Virology, 79:2346-2355); and (5) RP7, a subgenomic construct of genotype 1b (Elazar et al., 2003, Journal of Virology 77:6055-6061).

Antiviral activity for each test compound was determined as previously described (Okuse et al., 2005, Antiviral Research 65:23-34). Briefly, replicon cell lines were maintained as sub-confluent cultures on 96-well plates. Compounds were added daily for three days in fresh medium. Twenty-four hours after the last dose of compound, antiviral activity was determined by blot hybridization analysis of intracellular HCV RNA, and cytotoxicity was assessed by neutral red dye uptake. $EC_{50}$, $EC_{90}$, $CC_{50}$ and selectivity index were calculated for each compound tested in a replicon cell line. $EC_{50}$=drug concentration producing a 50% reduction of intracellular HCV RNA relative to the average levels in untreated cultures. $EC_{90}$=drug concentration producing a 90% reduction of intracellular HCV RNA relative to the average levels in untreated cultures. $CC_{50}$=drug concentration producing a 50% reduction of neutral red dye uptake relative to the average levels in untreated cultures. Selectivity index=$CC_{50}$ divided by $EC_{50}$. $EC_{50}$, $EC_{90}$ and $CC_{50}$ values (±standard deviations [S.D.]) were calculated by linear regression analysis using data combined from all treated cultures. Median $EC_{50}$ and $EC_{90}$ values were calculated for each compound based on the results for determined for the five different replicon cell lines.

Nitazoxanide and tizoxanide were provided by Romark Laboratories, L.C. (Tampa, Fla. USA). Recombinant interferon α-2b was purchased from PBL Biomedical Laboratories (Piscataway, N.J. USA). Ribavirin was purchased from Sigma-Aldrich (St. Louis, Mo. USA). 2'-C-methyl cytidine (Pierra, et al. 2005, Nucleosides Nucleotides Nucleic Acids, 24:767-770) was purchased from Moraveck Biochemicals, Inc. (La Brea, Calif. USA). Interferon α-2b was solubilized and/or diluted in sterile phosphate-buffered saline (PBS)/1% BSA as instructed by the manufacturer. Ribavirin, nitazoxanide, tizoxanide and 2'-C-methyl cytidine were solubilized in 100% tissue culture grade DMSO (Sigma). Stock solutions were stored (−70° C. for interferon α-2b, −20° C. for nitazoxanide, tizoxanide, ribavirin and 2'C-methyl cytidine) in quantities sufficient for a single experiment and used only once. Daily aliquots of test compounds were made from the stock solutions in individual tubes and stored at the appropriate temperatures. On each day of treatment, daily aliquots of the test compounds were suspended into culture medium at room temperature, and immediately added to the cell cultures, thereby subjecting each aliquot of test compound to the same, limited, number of freeze-thaw cycles.

Nitazoxanide and tizoxanide selectively reduced intracellular HCV replication in each of the five HCV genotype 1-derived replicon cell lines (Table 1). Median $EC_{50}$s were 0.13 μM and 0.15 μM for nitazoxanide and tizoxanide, respectively, compared to 0.86 IU/mL for interferon α-2b, 69 μM for ribavirin and 2.1 μM for 2'-C-methyl cytidine.

TABLE 1

Relative potency of test compounds against HCV replication.

| Drug<br>Cell line | $EC_{50}$ (μM) | $EC_{90}$ (μM) | $CC_{50}$ (μM) | S.I.[1] |
|---|---|---|---|---|
| Nitazoxanide | | | | |
| AVA5 | 0.13 ± 0.02 | 1.0 ± 0.2 | 39 ± 3.9 | 300 |
| H/FL-Neo | 0.33 ± 0.05 | 1.1 ± 0.1 | 49 ± 1.5 | 149 |
| JWT | 0.11 ± 0.01 | 1.0 ± 0.2 | 39 ± 1.0 | 354 |
| 4-3-10 | 0.10 ± 0.03 | 0.87 ± 0.16 | 34 ± 0.4 | 340 |
| RP7 | 0.16 ± 0.01 | 1.2 ± 0.1 | 38 ± 0.8 | 238 |
| Median | 0.13 | 1.0 | | |
| Tizoxanide | | | | |
| AVA5 | 0.12 ± 0.01 | 0.77 ± 0.10 | 25 ± 2.8 | 208 |
| H/FL-Neo | 0.25 ± 0.03 | 1.0 ± 0.1 | 4.2 ± 0.2 | 17 |
| JWT | 0.16 ± 0.02 | 0.76 ± 0.03 | 24 ± 2.9 | 150 |
| 4-3-10 | 0.11 ± 0.05 | 0.55 ± 0.08 | 21 ± 1.1 | 191 |
| RP7 | 0.15 ± 0.01 | 0.94 ± 0.10 | 25 ± 1.0 | 167 |
| Median | 0.15 | 0.77 | | |
| Interferon α-2b (IU/ml) | | | | |
| AVA5 | 1.5 ± 0.2 | 8.2 ± 0.8 | >10000 | >6667 |
| H/FL-Neo | 2.1 ± 0.2 | 9.4 ± 0.9 | >10000 | >4762 |
| JWT | 0.77 ± 0.03 | 2.6 ± 0.2 | >10000 | >12987 |
| 4-3-10 | 0.86 ± 0.06 | 5.7 ± 0.4 | >10000 | >11627 |
| RP7 | 0.41 ± 0.01 | 3.6 ± 0.2 | >10000 | >24390 |
| Median | 0.86 | 5.7 | | |
| Ribavirin | | | | |
| AVA5 | 70 ± 0.5 | 220 ± 34 | 84 ± 4.7 | 1.2 |
| H/FL-Neo | | | | |
| JWT | 23 ± 2.2 | 62 ± 1.7 | 89 ± 7.5 | 3.9 |
| 4-3-10 | | | | |
| RP7 | 69 ± 4.4 | 122 ± 13 | 77 ± 4.9 | 1.2 |
| Median | 69 | 122 | | |
| 2'-C-methyl cytidine | | | | |
| AVA5 | 2.1 ± 0.2 | 8.1 ± 0.7 | >300 | >143 |
| H/FL-Neo | 1.8 ± 0.2 | 8.1 ± 0.8 | >1000 | >556 |
| JWT | 2.2 ± 0.1 | 8.2 ± 0.7 | >300 | >136 |
| 4-3-10 | 2.1 ± 0.1 | 8.0 ± 0.9 | >300 | >143 |
| RP7 | 2.0 ± 0.1 | 9.0 ± 0.6 | >300 | >150 |
| Median | 2.1 | 8.1 | | |

[1]S.I. (Selectivity Index) = $CC_{50}/EC_{50}$

Example 2

Synergistic Activity of Nitazoxanide and Tizoxanide with Other Anti-HCV Drugs Activity of combination treatments with nitazoxanide plus interferon α-2b, tizoxanide plus interferon α-2b, nitazoxanide plus 2'-C-methyl cytidine and tizoxanide plus 2'-C-methyl cytidine against HCV replication were evaluated in the AVA5 replicon cell line using the methods previously described (Okuse et al., 2005, Antiviral Research 65:23-34). Analyses of interactions between compounds used in combination treatments were performed using Calcusyn™ software (Biosoft, Cambridge, UK).

Figure 1B:
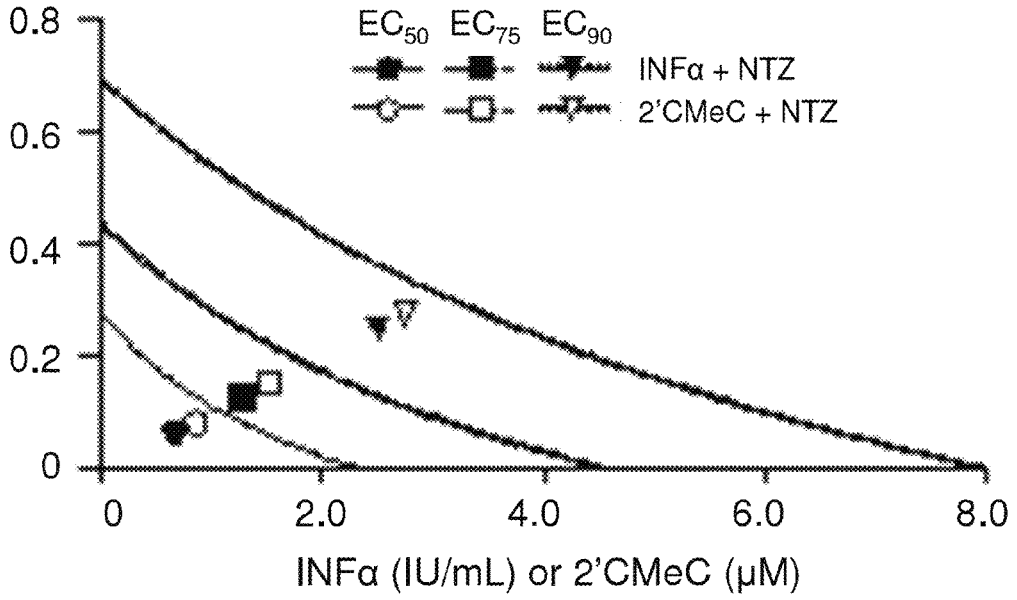

Combinations of nitazoxanide with either interferon α-2b or 2'-C-methyl cytidine and tizoxanide with either interferon α-2b or 2'-C-methyl cytidine exhibited synergistic interactions against HCV replication (Table 2, FIGS. 1a and 1b). In FIGS. 1a and 1b analyses of interactions between compounds in combination treatments are shown.

TABLE 2

Relative potency of combination treatments against HCV replication in AVA5 cell cultures.

| Treatment | $EC_{50}$ (μM) | $EC_{90}$ (μM) | $CC_{50}$ (μM) | S.I.[1] |
|---|---|---|---|---|
| Nitazoxanide (NTZ) | 0.21 ± 0.03 | 0.93 ± 0.11 | 38 ± 1.8 | 181 |
| Tizoxanide (TIZ) | 0.15 ± 0.02 | 0.81 ± 0.92 | 15 ± 1.2 | 100 |
| IFNα-2b | 1.9 ± 0.22 | 8.9 ± 0.92 | >100002 | >5263 |
| 2'-C-methyl cytidine (2'CMeC) | 1.6 ± 0.2 | 8.3 ± 0.7 | >300 | >188 |
| 2'CMeC + IFNα-2b, 1:1 | 0.67 ± 0.007 | 2.3 ± 0.3 | >300 | >448 |
| NTZ + IFNα-2b, 1:10 | 0.06 ± 0.008 | 0.25 ± 0.03 | 33 ± 1.3 | 550 |
| NTZ + 2'CMeC, 1:10 | 0.07 ± 0.005 | 0.28 ± 0.02 | 35 ± 1.5 | 500 |
| TIZ + IFNα-2b, 1:10 | 0.07 ± 0.01 | 0.22 ± 0.03 | 17 ± 1.3 | 245 |
| TIZ + 2'CMeC, 1:10 | 0.06 ± 0.004 | 0.19 ± 0.02 | 18 ± 1.1 | 300 |

[1]SI = $CC_{50}/EC_{50}$.
[2]Values for IFNα-2b expressed in IU/mL

FIG. 1a presents CI-Fa (Combination Index-Fraction (of virus) affected) plots (Belen'kii and Schinazi, 1994, Antiviral Research 25:11-18). For these plots, a combination index [CI] greater than 1.0 indicates antagonism and a CI less than 1.0 indicates synergism. Evaluations of synergy, additivity (summation), or antagonism at different levels of virus inhibition (e.g. 5%, or Fa=0.05 to 99%, or Fa=0.99) are provided by the plotted lines and points. FIG. 1b shows conservative isobolograms. For these plots, $EC_{50}$, $EC_{75}$, and $EC_{90}$ (50%, 75%, and 90% effective antiviral concentrations) values for the combination treatments are displayed as single points. Three lines radiating out from the axes denote the expected (e.g. additive) $EC_{50}$, $EC_{75}$, and $EC_{90}$ values for drug combinations as calculated from the monotherapies. $EC_{50}$, $EC_{75}$, and $EC_{90}$ values for the combinations that plot to the left (e.g. less than) of the corresponding lines indicate synergy, and values plotting to the right (e.g. greater than) of the corresponding lines indicate antagonism.

Example 3

Enhanced Activity of Interferon Alpha+Nitazoxanide after Pre-Treatment with Nitazoxanide To evaluate the effect of pre-treating with nitazoxanide prior to treatment with combination treatments, cultures were treated for either 3 or 6 days with nitazoxanide, interferon α-2b, or 2'-C-methyl cytidine or combinations of nitazoxanide and either interferon α-2b or 2'-C-methyl cytidine. Alternatively, cultures were treated with nitazoxanide for 3 days, followed by an additional 3 days of treatment with a combination of nitazoxanide and either interferon α-2b or 2'-C-methyl cytidine. Antiviral activity and cytotoxicity was determined 24 hours after the end of each respective treatment as described previously.

Figure 2A:
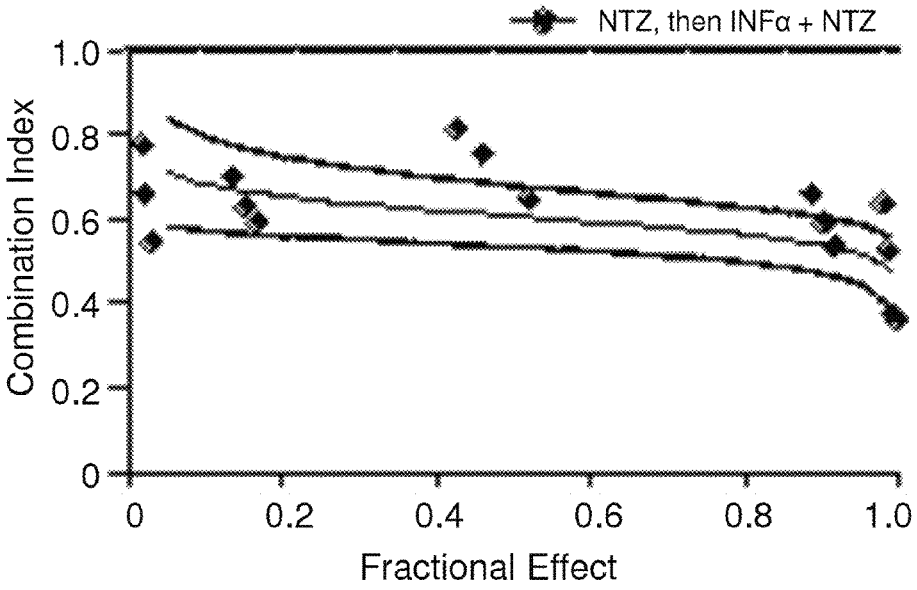
FIGS. 2a and 2b are graphs illustrating synergistic activity when an HCV replicon-containing cell line is treated first with nitazoxanide and then with nitazoxanide plus interferon alpha-2b.
Figure 2B:
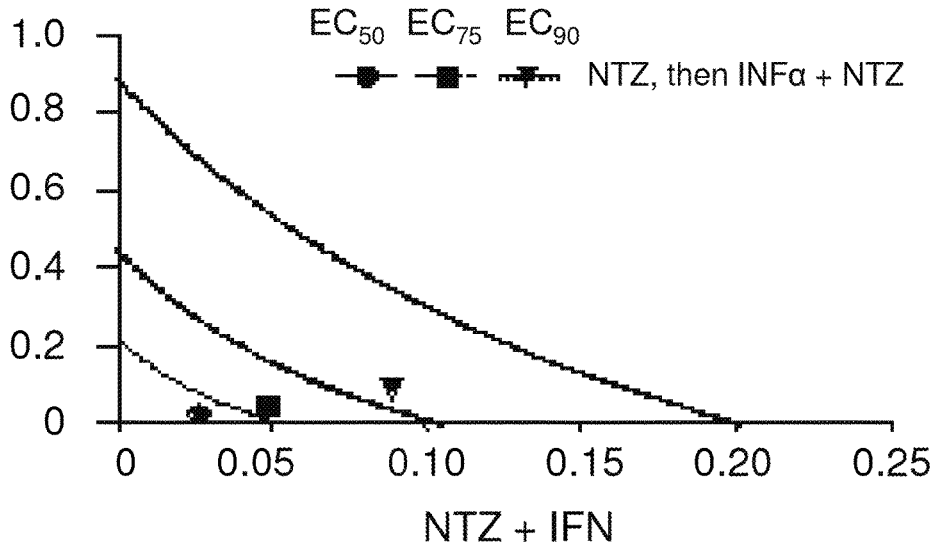

Pre-treatment with nitazoxanide improved the potency of combination treatment with nitazoxanide plus interferon α-2b by approximately 3-fold (Table 3 and FIGS. 2a and 2b). Pre-treatment did not, however, affect the potency of combination treatment with 2'-C-methyl cytidine (Table 4). FIGS. 2a and 2b show analyses of the effect in cultures pre-treated with nitazoxanide before treatment with nitazoxanide plus interferon α-2b. Analyses were performed using Calcusyn™ software (Biosoft, Cambridge, UK). Two types of evaluations are presented. FIG. 2a presents CI-Fa (Combination Index-Fraction (of virus) affected) plots (Belen'kii and Schinazi, 1994). For these plots, a combination index [CI] greater than 1.0 indicates antagonism and a CI less than 1.0 indicates synergism. Evaluations of synergy, additivity (summation), or antagonism at different levels of virus inhibition (e.g. 5%, or Fa=0.05 to 99%, or Fa=0.99) are provided by the plotted lines and points. Dotted lines indicate 1.96 standard deviations (not shown in FIG. 1a for clarity). FIG. 2b presents conservative isobolograms. For these plots, $EC_{50}$, $EC_{75}$, and $EC_{90}$ (50%, 75%, and 90% effective antiviral concentrations) values for the combination treatments are displayed as single points. Three lines radiating out from the axes denote the expected (e.g. additive) $EC_{50}$, $EC_{75}$, and $EC_{90}$ values for drug combinations as calculated from the monotherapies. $EC_{50}$, $EC_{75}$, and $EC_{90}$ values for the combinations that plot to the left (e.g. less than) of the corresponding lines indicate synergy, and values plotting to the right (e.g. greater than) of the corresponding lines indicate antagonism.

TABLE 3

Effect of NTZ Pretreatment on Activity of NTZ + IFNα Combination Treatment

| Treatment | Duration (days) | NTZ (μM) $EC_{50}$ (μM) | NTZ (μM) $EC_{90}$ (μM) | IFNα-2b (IU/mL) $EC_{50}$ (μM) | IFNα-2b (IU/mL) $EC_{90}$ (μM) |
|---|---|---|---|---|---|
| IFNα | 3 | | | 1.9 ± 0.3 | 8.3 ± 0.9 |
| IFNα | 6 | | | 1.7 ± 0.2 | 7.8 ± 0.8 |
| NTZ | 3 | 0.22 ± 0.03 | 1.0 ± 0.1 | | |
| NTZ | 6 | 0.20 ± 0.02 | 0.92 ± 0.10 | | |
| NTZ + IFNα, 1:10 | 3 | 0.08 ± 0.010 | 0.27 ± 0.03 | 0.82 ± 0.07 | 2.7 ± 0.3 |
| NTZ + IFNα, 1:10 | 6 | 0.09 ± 0.010 | 0.24 ± 0.04 | 0.75 ± 0.09 | 2.4 ± 0.2 |
| NTZ, then NTZ + IFNα | 6 | 0.03 ± 0.004 | 0.09 ± 0.011 | 0.31 ± 0.04 | 0.96 ± 0.12 |

TABLE 4

Effect of NTZ Pretreatment on Activity of NTZ + 2'CMeC Combination Treatment

| Treatment | Duration (days) | NTZ (μM) $EC_{50}$ (μM) | NTZ (μM) $EC_{90}$ (μM) | 2'CMeC (μM) $EC_{50}$ (μM) | 2'CMeC (μM) $EC_{90}$ (μM) |
|---|---|---|---|---|---|
| 2'CMeC | 3 | | | 1.7 ± 0.2 | 6.2 ± 0.5 |
| 2'CMeC | 6 | | | 1.3 ± 0.2 | 5.8 ± 0.9 |
| NTZ | 3 | 0.22 ± 0.03 | 1.0 ± 0.1 | | |
| NTZ | 6 | 0.20 ± 0.02 | 0.92 ± 0.10 | | |
| NTZ + 2'CMeC, 1:10 | 3 | 0.05 ± 0.006 | 0.16 ± 0.02 | 0.57 ± 0.07 | 1.8 ± 0.2 |

TABLE 4-continued

Effect of NTZ Pretreatment on Activity of NTZ + 2'CMeC Combination Treatment

| Treatment | Duration (days) | NTZ (μM) $EC_{50}$ (μM) | NTZ (μM) $EC_{90}$ (μM) | 2'CMeC (μM) $EC_{50}$ (μM) | 2'CMeC (μM) $EC_{90}$ (μM) |
|---|---|---|---|---|---|
| NTZ + 2'CMeC, 1:10 | 6 | 0.05 ± 0.007 | 0.17 ± 0.03 | 0.54 ± 0.06 | 1.9 ± 0.2 |
| NTZ, then NTZ + 2'CMeC | 6 | 0.06 ± 0.005 | 0.15 ± 0.02 | 0.58 ± 0.08 | 1.7 ± 0.3 |

Example 4

Enhanced Activity of Interferon Alpha after Pre-Treatment with Nitazoxanide or Tizoxanide To evaluate the effect of interferon alpha following pre-treatment with nitazoxanide or tizoxanide, a parental replicon-containing cell line (RP-7) was serially passaged in increasing concentrations of nitazoxanide or tizoxanide. Anti-HCV activity of interferon alpha-2b was determined using the parental cell line and using the cell lines obtained after passage in nitazoxanide or tizoxanide. Anti-HCV activity was determined by the methods described above.

The parental replicon-containing cell line was established by electroporation of RNA transcribed in vitro off of the Sca-I-linearized Bart 79I plasmid into Huh-7 cells (Elazar et al., 2003). Bart79I encodes for a second-generation high-efficiency bi-cistronic sub-genomic replicon of genotype 1b containing a single adaptive mutation (S1179I) in the NS5A gene, and the neomycinphosphotransferase gene in the first cistron. The electroporated cells were plated along with naïve Huh-7 feeder cells and grown in medium—DMEM (4.5 g/l glucose, L-glutamine and sodium pyruvate—Mediatech 10-013-CV), 10% fetal bovine serum, 1% Penicillin-streptomycin, 1% L-glutamine (final concentration 2 mM), 1×MEM Non-Essential Amino Acids (100×) (Invitrogen)—and 1 mg/ml G418. After 3 weeks, G418-resistant colonies appeared. One of the resulting colonies was isolated, expanded, passaged in 700 μg/ml G418, and termed RP-7.

RP-7 cells were subjected to a resistance-promoting regimen as follows. The cells were grown in the medium described above containing 700 μg/ml G418 (Invitrogen), 1% tissue culture grade DMSO (Sigma), and an initial low concentration of nitazoxanide or tizoxanide which was then steadily increased every week, with an intervening 2-day drug holiday in between each dose increase. On days 1 through 5 of each dose of drug, the media was changed daily to provide a source of fresh drug. No media changes were performed on days 6 and 7 (the drug holiday). The initial concentration of nitazoxanide or tizoxanide was 0.02 μM, followed by 0.05 μM. 0.1 μM, 0.5 μM, 1 μM, and subsequent weekly increases of 1 μM. A final concentration of 11 μM was used for the cells passaged in nitazoxanide while a final concentration of 8 μM was used for cells passaged in tizoxanide. The resulting cells were subsequently passaged at this final concentration for at least 2 months prior to being used to test the anti-HCV activity of interferon alpha-2b.

Results are presented in Table 5. Serial passage of the parental cell line in increasing concentrations of nitazoxanide or tizoxanide did not induce resistance to interferon alpha-2b. The cell lines passaged in nitazoxanide or tizoxanide were actually 2.5 to 7.6-fold more susceptible to interferon alpha-2b than the parental replicon-containing cell line, which was not passaged in nitazoxanide or tizoxanide.

TABLE 5

Potency of Interferon α-2b Against HCV Replication in RP7 Cells Before and After Serial Passage in Increasing Concentrations of Nitazoxanide and Tizoxanide

| Cell line | $EC_{50}$ (μM) | $EC_{90}$ (μM) | $CC_{50}$ (μM) | SI |
|---|---|---|---|---|
| Parental cell line (RP-7) | 0.41 ± 0.01 | 3.6 ± 0.2 | >10000 | >24390 |
| RP7 cells passaged in nitazoxanide | 0.11 ± 0.02 | 0.47 ± 0.04 | >10000 | >90909 |
| RP7 cells passaged in tizoxanide | 0.16 ± 0.01 | 0.42 ± 0.04 | >10000 | >62500 |

Example 5

Figure 3:
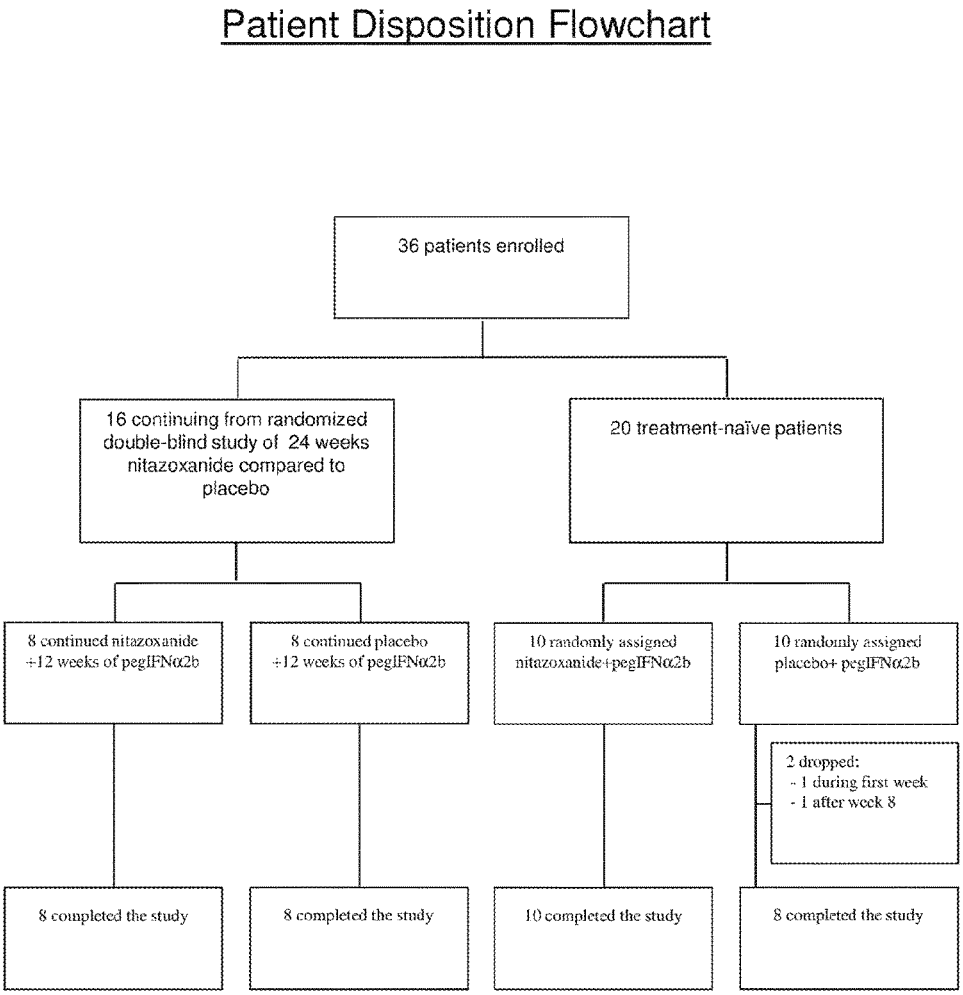
FIG. 3 is a patient disposition chart showing the selection of participants for the experiment described in Example 5.

Treatment of Chronic Hepatitis C with a Combination of Nitazoxanide and Tizoxanide Fifty (50) patients were enrolled in a double-blind study of Alinia® (pharmaceutical composition comprising 99% nitazoxanide and 1% tizoxanide as active agents) administered orally as a 500 mg tablet twice daily for 24 weeks compared to a placebo in treating patients with chronic hepatitis C genotype 4. The 50 patients were enrolled at three study sites in Egypt: 32 at Cairo, 12 at Alexandria and 6 at Tanta. Three patients dropped out of the study immediately after enrollment and did not return for any post-treatment follow-up. One patient did not return for follow-up after week 12. Each of the remaining 46 patients completed the study. See FIG. 3 for a Patient Disposition Flowchart. One patient was co-infected with hepatitis B virus. The patient was HBeAg-negative, and an exception was made to allow enrollment of this patient. The protocol called for use of an intent-to-treat population (all patients randomized) for the primary efficacy analysis. The three patients that dropped out before receiving any medication were excluded from the efficacy analysis. The patient who dropped out after week 12 was included in the efficacy analysis and analyzed on the basis of last observation carried forward. Demographic and disease-related characteristics for the 47 patients included in the efficacy analysis is summarized by treatment group in Table 6.

At each study visit, the patients were questioned regarding treatment compliance. With one exception, each of the patients completing the study reported that they had been compliant with taking the medication. One patient completed the study but reported sporadic noncompliance with taking medication due to abdominal pain.

TABLE 6

Demographic and Disease-Related Characteristics

| | All Subjects | Active | Placebo | P[1] |
|---|---|---|---|---|
| Race: | | | | |
| Caucasian | 47 | 23 | 24 | 1.0 |
| Gender: | | | | |
| Male/Female | 39/8 | 19/4 | 20/4 | 1.0 |

TABLE 6-continued

Demographic and Disease-Related Characteristics

| | All Subjects | Active | Placebo | P[1] |
|---|---|---|---|---|
| Age (years): | | | | |
| Mean ± SD | 47.3 ± 9.3 | 49.7 ± 8.4 | 45.0 ± 9.6 | .08 |
| Median (Range) | 48 (27-67) | 51 (35-67) | 46 (27-64) | |
| Weight (kgs): | | | | |
| Mean ± SD | 86.2 ± 18.8 | 84.8 ± 16.7 | 87.5 ± 21.0 | .62 |
| Median (Range) | 84 (64-143) | 84 (64-130) | 82 (65-143) | |
| Body Mass Index: | | | | |
| Mean ± SD | 29.4 ± 5.5 | 29.0 ± 5.1 | 29.8 ± 6.0 | .62 |
| Median (Range) | 28.2 (21-47) | 27.3 (22-47) | 28.3 (21-46) | |
| Viral load (log10 IU/mL): | | | | |
| Mean ± SD | 5.2 ± 0.7 | 5.3 ± 0.7 | 5.2 ± 0.8 | .43 |
| Median (Range) | 5.3 (3.5-6.5) | 5.4 (4.0-6.3) | 5.3 (3.5-6.5) | |
| Viral load >800,000 IU/mL | 10 | 6 | 4 | .49 |
| Elevated ALT | 31 | 13 | 18 | .23 |
| Necroinflammatory score: | | | | |
| Mean ± SD | 6.0 ± 3.2 | 6.3 ± 3.3 | 5.7 ± 2.7 | .51 |
| Median (Range) | 5 (2-17) | 5 (3-17) | 5.5 (2-11) | |
| Liver disease: | | | | |
| No fibrosis | 8 | 4 | 4 | .95 |
| Fibrous portal expansion | 18 | 8 | 10 | |
| Bridging fibrosis | 14 | 7 | 7 | |
| Cirrhosis (compensated) | 3 | 1 | 2 | |
| Cirrhosis (decompensated) | 4 | 3 | 1 | |
| Previously treated with peginterferon/ribavirin | 5 | 3 | 2 | .67 |
| Diabetes mellitus | | | | |
| Controlled | 7 | 4 | 3 | .70 |
| Uncontrolled | 3 | 1 | 2 | 1.0 |

[1]Fisher's exact test or chi-square test used for comparing proportions, t-test for means.

Virologic responses are summarized by treatment group in Table 7. The proportion of virologic responders in the active treatment group was significantly higher than in the placebo treatment group (P=0.0039). Virologic responses (undetectable serum HCV RNA) were observed at weeks 4 (n=3), week 8 (n=3) and week 20 (n=1). Each of these responses were maintained throughout the treatment period.

TABLE 7

Virologic Responses by Treatment Group

| | Active | Placebo | P[1] |
|---|---|---|---|
| Responders/Total (%) | 7/23 (30.4%) | 0/24 (0%) | 0.0039 |

[1]two-sided Fisher's exact test

Demographic characteristics, baseline laboratory data, data from liver biopsies and medical histories were evaluated to identify independent predictors of virologic response within the active treatment group. Predictors of response are listed in Table 8. The most significant predictor of response was lower viral load at baseline. All responders had baseline viral loads≤384,615 IU/mL. Laboratory values at baseline (platelet counts, prothrombin time and alfa fetoprotein) also suggested that the responders had less severe liver disease.

TABLE 8

| Independent Predictors of Response | |
|---|---|
| Predictors of Response | P |
| Lower viral load at baseline | .0086 |
| Indicators of less serious liver disease | |
| Higher platelet counts | .0385 |
| Lower prothrombin time | .0579 |
| Lower alfa fetoprotein | .0696 |

Further analysis of patients with complicating disease-related factors such as high viral loads, cirrhosis, uncontrolled diabetes mellitus or hepatitis B co-infection showed very poor response rates in these subsets of patients (see Table 9). Fifteen (15) of the 16 Alinia® treatment failures had high viral load, advanced liver disease, uncontrolled diabetes mellitus or hepatitis B virus co-infection. The Alinia® responders can, therefore, be described as patients with low viral loads (<800,000 IU/mL) whose disease had not advanced to cirrhosis and who did not have uncontrolled diabetes mellitus or hepatitis B virus co-infection. Two (2) virologic responders in the active treatment group had a prior history of treatment with peginterferon/ribavirin. One was unable to tolerate peginteferon/ribavirin and discontinued therapy after 5 weeks. The other relapsed following completion of 48 weeks of peginterferon/ribavirin.

TABLE 9

| Response Rates in Patients with Complicating Disease-Related Factors | |
|---|---|
| Complicating disease-related factors | Responders/ Total |
| High viral load (>800,000 IU/mL) | 0/3 |
| Advanced liver disease: cirrhosis | 0/3 |
| Advanced liver disease: bridging fibrosis | 3/5 |
| Uncontrolled diabetes mellitus | 0/3 |
| Hepatitis B virus co-infection | 0/1 |
| High viral load and cirrhosis | 0/1 |
| High viral load and bridging fibrosis | 0/1 |
| High viral load, uncontrolled diabetes and bridging fibrosis | 0/1 |

Sustained Virologic Response: The 7 virologic responders were followed up at least 24 weeks after the end of treatment, and 5 of these patients had a sustained virologic response (undetectable serum HCV RNA) at follow-up. Sustained virologic response rates are presented by treatment group in Table 10. Two patients failed to maintain their virologic responses off-treatment. One patient only completed 8 weeks of treatment. One patient completed the study, but reported sporadic noncompliance with taking medication due to abdominal pain. Each of these two patients had advanced liver disease (bridging fibrosis).

TABLE 10

| Sustained Virologic Responses by Treatment Group | | | |
|---|---|---|---|
| | Active | Placebo | P* |
| Responders/Total (%) | 5/23 (21.7%) | 0/24 (0%) | 0.0219 |

*two-sided Fisher's exact test

Figure 4:
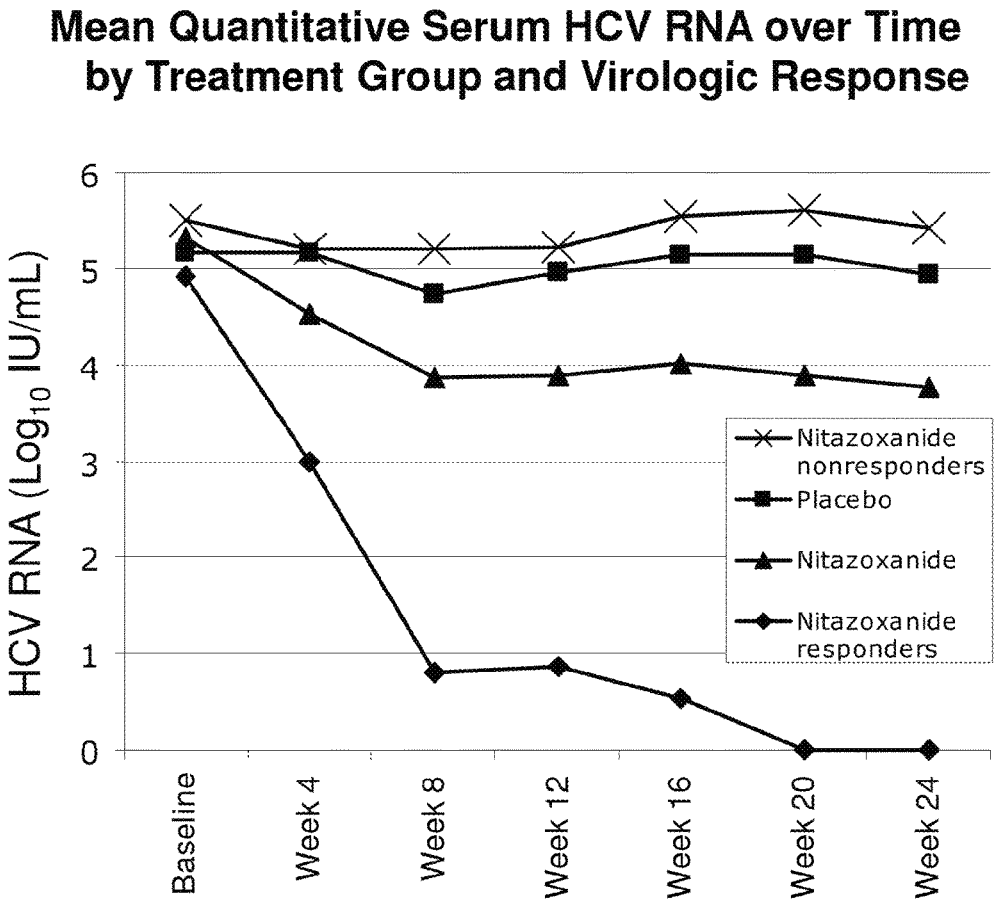
FIG. 4, described in Example 5, is a graph showing mean quantitative serum HCV RNA levels over time for different treatment groups.
Figure 5:
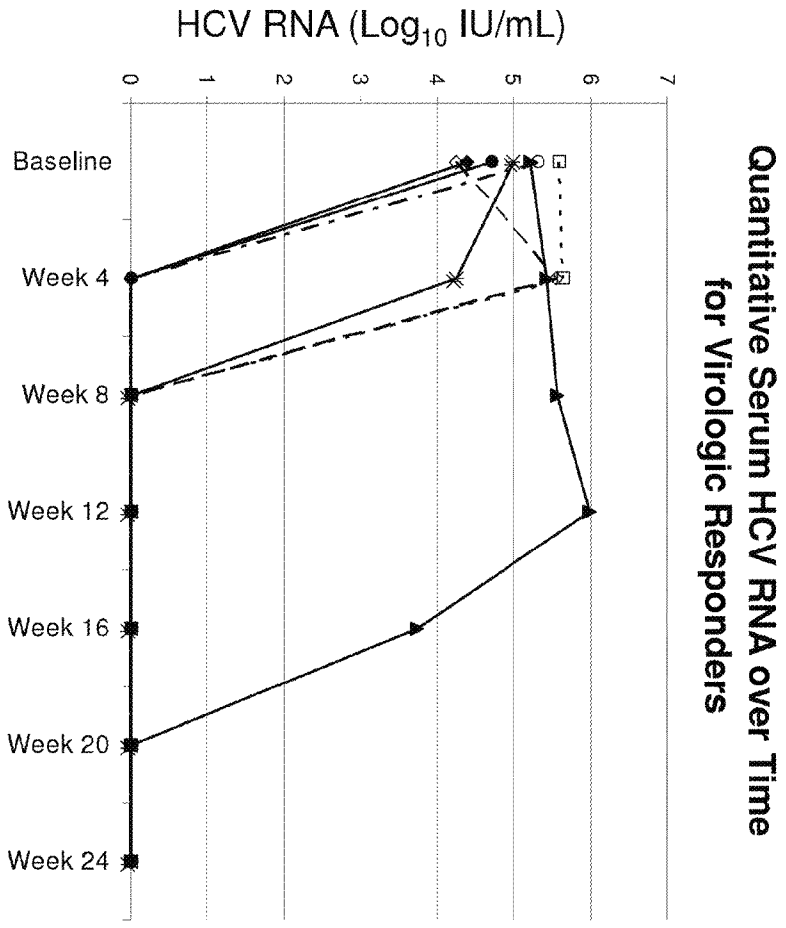
FIG. 5, described in Example 5, is a graph showing quantitative serum HCV RNA levels over time for different patients.

Changes in Quantitative Serum HCV RNA (Viral Load): Mean quantitative viral loads for the active treatment group, the placebo treatment group, active treatment group virologic responders, and active treatment group virologic failures are presented in Table 11 and FIG. 4. Reduction of the mean quantitative viral load from baseline to end of treatment was significantly greater for the active treatment group (reduction of 1.55±2.34 $\log_{10}$ IU/mL) than for the placebo group (reduction of 0.21±0.98 $\log_{10}$ IU/mL) observed for the placebo treatment group (P=0.0166, t-test). The reduction in mean viral load observed for the active treatment group was entirely attributed to the virologic responders. Changes in viral loads of nonresponders were not significantly different than changes noted for the placebo treatment group. Actual quantitative viral loads for the 7 virologic responders over time are presented in Table 12 and FIG. 5.

TABLE 11

| Mean Quantitative Serum HCV RNA over Time by Treatment Group and Virologic Response ($Log_{10}$ IU/mL) | | | | | | | |
|---|---|---|---|---|---|---|---|
| | Baseline | Week 4 | Week 8 | Week 12 | Week 16 | Week 20 | Week 24 |
| Alinia Non-responsders | 5.5 | 5.21 | 5.21 | 5.23 | 5.54 | 5.61 | 5.42 |
| Placebo | 5.16 | 5.17 | 4.73 | 4.96 | 5.15 | 5.13 | 4.94 |
| Alinia | 5.33 | 4.53 | 3.87 | 3.9 | 4.02 | 3.9 | 3.77 |
| Alinia Responders | 4.92 | 2.98 | 0.80 | 0.85 | 0.53 | * | * |

* All values below lower limit of detection (10 IU/mL)

TABLE 12

| Quantitative Serum HCV RNA over Time for Virologic Responders ($Log_{10}$ IU/mL) | | | | | | | |
|---|---|---|---|---|---|---|---|
| Patient | Baseline | Week 4 | Week 8 | Week 12 | Week 16 | Week 20 | Week 24 |
| #1 | 4.37 | * | * | * | * | * | * |
| #6 | 5.59 | 5.64 | * | * | * | * | * |
| #15 | 5.22 | 5.43 | 5.57 | 5.98 | 3.74 | * | * |
| #17 | 5.30 | * | * | * | * | * | * |
| #21 | 5.00 | 4.23 | * | * | * | * | * |
| #37 | 4.70 | * | * | * | * | * | * |
| #40 | 4.25 | 5.56 | * | * | * | * | * |

* Below limit of detection (10 IU/mL)

Changes in ALT: Mean changes in ALT from baseline to end of treatment were not significantly different for the two treatment groups (−3.9±32 for the active treatment group and −1.3±42 for the placebo group, P=0.82, t test). Categorical changes in ALT from baseline to end of treatment are summarized by treatment group in Table 13. Three of the virologic responders in the active treatment group had normal ALT values at baseline, which remained normal at the end of treatment. One of the four virologic responders with elevated ALT at baseline had normal ALT at the end of treatment while the ALT for the other 3 remained elevated. Four of the five patients with sustained virologic responses also had normal ALT after 24 weeks off-treatment.

TABLE 13

| Change in ALT from Baseline to End of Treatment | | |
|---|---|---|
| | Active | Placebo |
| Normalized | 3 | 2 |
| Remained Normal | 7 | 4 |
| Remained Elevated | 10 | 16 |
| Normal to Elevated | 3 | 2 |

Quantitative HCV RNA values were missing for one patient at week 24 and for one patient at weeks 12, 16, 20 and 24. End of treatment data for these patients was analyzed using the last data point available (last observation carried forward). An interim analysis of end of treatment virologic response was conducted for the first 21 patients enrolled in the study. For purposes of this report, no adjustments have been made to account for multiple analyses.

Virologic response rates are presented by treatment group by study center in Table 14. The higher response rate observed in the active treatment group for the Cairo study center is attributed to disease-related characteristics of patients enrolled at the different sites. Each of the 9 patients enrolled in the active treatment group at the Alexandria and Tanta centers had high viral loads (>800,000 IU/mL), advanced liver disease, uncontrolled diabetes mellitus or hepatitis B virus co-infection.

TABLE 14

Virologic Response by Treatment Group and Study Center

| | Cairo | Alexandria | Tanta |
|---|---|---|---|
| Active | 7/14 (50%) | 0/6 (0%) | 0/3 (0%) |
| Placebo | 0/15 (0%) | 0/6 (0%) | 0/3 (0%) |

P = 0.0453, Cochran-Mantel-Haenszel test

A summary of response rates for the active treatment group by disease-related complications and study center is presented in Table 15.

TABLE 15

Response Rates for the Active Treatment Group by Complicating Disease-Related Factors and Study Center

| | Study Center | | |
|---|---|---|---|
| Complicating factors | Cairo | Alexandria | Tanta |
| High viral load | 0/1 | 0/2 | — |
| Cirrhosis | 0/2 | — | 0/1 |
| Bridging fibrosis | 3/4 | — | 0/1 |
| Uncontrolled diabetes mellitus | 0/1 | 0/2 | — |
| Hepatitis B virus co-infection | — | 0/1 | — |
| High viral load and cirrhosis | — | 0/1 | — |
| High viral load + bridging fibrosis | 0/1 | — | — |
| High viral load, diabetes, bridging fibrosis | — | — | 0/1 |
| Patients without complicating factors | 4/5 | — | — |
| Totals | 7/14 | 0/6 | 0/3 |

There were no significant protocol deviations that would warrant an efficacy subset analysis. An analysis of the subset of patients with low viral loads and no cirrhosis, uncontrolled diabetes or hepatitis B virus co-infection is presented in Table 16.

TABLE 16

Virologic Responses by Treatment Group, Subset of Patients with Low Viral Loads and No Cirrhosis, Uncontrolled Diabetes or Hepatitis B Co-infection

| | Active | Placebo | P* |
|---|---|---|---|
| Responders/Total (%) | 7/10 (70%) | 0/15 (0%) | 0.0002 |

*two-sided Fisher's exact test

The Alinia® tablets administered 500 mg twice daily with food for 24 weeks produced virologic responses (undetectable serum HCV RNA) in 7 of 23 patients (30.4%) compared to zero of 25 patients (0%) from the placebo group (P=0.0039).

The virologic responses occurred between 4 and 20 weeks of treatment (3 at week 4, 3 at week 8, 1 at week 20) and were maintained through the end of treatment with no virological breakthroughs.

Virologic response was sustained in 5 of 23 patients in the Alinia® treatment group at least 24 weeks after the end of treatment (P=0.0219). Each of the two patients that relapsed following the end of treatment visit had advanced liver disease (bridging fibrosis). One dropped out of the study after 8 weeks of treatment, and the other reported sporadic noncompliance with taking the study medication.

Low viral load was the most significant independent predictor of virologic response (P=0.0086). None of the patients with cirrhosis, uncontrolled diabetes mellitus or hepatitis B virus co-infection responded to treatment.

When patients with high viral loads, cirrhosis, uncontrolled diabetes or hepatitis B co-infection were excluded from the efficacy analysis, virologic response rates were 7/10 (70%) for the active treatment group and 0/15 for the placebo group (P=0.0002). Two of the three Alinia®-treated failures included in this analysis had advanced liver disease with bridging fibrosis.

These results indicate that 24 weeks of Alinia® monotherapy is effective in achieving a sustained virologic response in patients with chronic hepatitis C genotype 4 when the patients have low viral loads and no other complicating factors such as cirrhosis, uncontrolled diabetes or hepatitis B co-infection.

Safety measures were examined in patients receiving Alinia® compared to patients receiving placebo tablets. The extent of exposure is summarized in Table 17. Three patients (2 randomized to the Alinia® treatment group, 1 randomized to the placebo group) dropped out of the study before returning for any follow-up visits. These patients did not report taking any medication or experiencing any adverse events, and they were excluded from the safety analyses.

TABLE 17

Extent of Exposure

| Treatment/Exposure | No. of Patients |
|---|---|
| Alinia 500 mg twice daily × 24 weeks | 22 |
| Alinia 500 mg twice daily × 12 weeks | 1 |
| Placebo twice daily × 24 weeks | 24 |

Sixteen patients (11 from Alinia® group, 5 from placebo group) reported a total of 33 adverse events. There were two serious adverse events. One patient in the placebo group experienced severe hematemesis and a patient in the Alinia® treatment group experienced moderate melena. Both events required hospitalization but resolved without discontinuing treatment. The remaining adverse events were mild to moderate and transient in nature, none requiring modification or discontinuation of treatment. Adverse events are displayed by body system, standard term, severity and causality in Table 18 for the active treatment group and in Table 19 for the placebo treatment group. The proportions of patients reporting each adverse event were compared by treatment group. There were no significant differences in the frequency or nature of adverse events reported by the two treatment groups.

TABLE 18

Adverse Events: Patients Exposed to Alinia ® (N = 23)

| Adverse event | Patients Reporting AEs | | Severity and Relationship to Use of the Drug[2] | | | | | | | | | | | |
|---|---|---|---|---|---|---|---|---|---|---|---|---|---|---|
| | | | Mild | | | | Moderate | | | | Severe | | | |
| (Affected system)[1] | Number | % | N | U | P | PR | N | U | P | PR | N | U | P | PR |
| Jaundice (DIG) | 2 | 8.7 | — | 2 | — | — | — | — | — | — | — | — | — | — |
| Anorexia (DIG) | 1 | 4.3 | — | — | 1 | — | — | — | — | — | — | — | — | — |
| Constipation (DIG) | 1 | 4.3 | — | 1 | — | — | — | — | — | — | — | — | — | — |
| Diarrhea (DIG) | 1 | 4.3 | — | 1 | — | — | — | — | — | — | — | — | — | — |
| Flatulence (DIG) | 1 | 4.3 | — | 1 | — | — | — | — | — | — | — | — | — | — |
| GI Disorder (DIG) | 1 | 4.3 | — | — | — | — | 1 | — | — | — | — | — | — | — |
| Melena (DIG) | 1 | 4.3 | — | — | — | — | — | 1 | — | — | — | — | — | — |
| Nausia (DIG) | 1 | 4.3 | — | 1 | — | — | — | — | — | — | — | — | — | — |
| Asthenia (BODY) | 4 | 17.4 | — | 4 | — | — | — | — | — | — | — | — | — | — |
| Pain Abdo (BODY) | 1 | 4.3 | — | 1 | — | — | — | — | — | — | — | — | — | — |
| Dysuria (UG) | 2 | 4.3 | — | 1 | — | — | — | 1 | — | — | — | — | — | — |
| Epistaxis (RES) | 1 | 4.3 | 1 | — | — | — | — | — | — | — | — | — | — | — |
| Palpitation (CV) | 1 | 4.3 | — | 1 | — | — | — | — | — | — | — | — | — | — |
| Myalgia (MS) | 1 | 4.3 | — | — | — | — | — | 1 | — | — | — | — | — | — |
| Somnolence (NER) | 1 | 4.3 | — | 1 | — | — | — | — | — | — | — | — | — | — |
| Skin Discolor (SKIN) | 1 | 4.3 | — | 1 | — | — | — | — | — | — | — | — | — | — |

[1]DIG = Digestive; BODY = Body as a whole or Nonspecific system; UG = Urogenital; RES = respiratory; CV = Cardiovascular; MS = Musculoskeletal; NER = Nervous; SKIN = Skin.
[2]Relationship to use of the drug: N = not related, U = unlikely related, P = possibly related, PR = probably related

TABLE 19

Adverse Events: Patients Exposed to Placebo (N = 24)

| Adverse event | Patients Reporting AEs | | Severity and Relationship to Use of the Drug[2] | | | | | | | | | | | |
|---|---|---|---|---|---|---|---|---|---|---|---|---|---|---|
| | | | Mild | | | | Moderate | | | | Severe | | | |
| (Affected system)[1] | Number | % | N | U | P | PR | N | U | P | PR | N | U | P | PR |
| Jaundice (DIG) | 1 | 4.2 | — | 1 | — | — | — | — | — | — | — | — | — | — |
| Hematemesis (DIG) | 1 | 4.2 | — | — | — | — | — | — | — | — | 1 | — | — | — |
| Vomit (DIG) | 1 | 4.2 | — | 1 | — | — | — | — | — | — | — | — | — | — |
| Asthenia (BODY) | 2 | 8.3 | — | 2 | — | — | — | — | — | — | — | — | — | — |
| Pain Abdo (BODY) | 2 | 8.3 | — | 2 | — | — | — | — | — | — | — | — | — | — |
| Headache (BODY) | 1 | 4.2 | — | 1 | — | — | — | — | — | — | — | — | — | — |
| Fever (BODY) | 1 | 4.2 | — | — | — | — | — | 1 | — | — | — | — | — | — |
| Urine Abnorm (UG) | 1 | 4.2 | — | 1 | — | — | — | — | — | — | — | — | — | — |
| Hemoptysis (RES) | 1 | 4.2 | — | 1 | — | — | — | — | — | — | — | — | — | — |
| Diabetes Mell (MAN) | 1 | 4.2 | — | 1 | — | — | — | — | — | — | — | — | — | — |

[1]DIG = Digestive; BODY = Body as a whole or Nonspecific system; UG = Urogenital; RES = respiratory; MAN = Metabolic and Nutritional.
[2]Relationship to use of the drug: N = not related, U = unlikely related, P = possibly related, PR = probably related Changes in laboratory safety parameters over time were analyzed by treatment group using repeated measures analysis of variance for continuous data and Fisher's Exact tests for categorical data. No significant changes in laboratory safety parameters were observed.

No safety concerns were identified during the course of this study. The Alinia® tablets administered 500 mg twice daily with food in patients with chronic hepatitis C were safe and well tolerated. Adverse events reported for patients treated with Alinia® tablets were similar to those reported by patients treated with placebo.

In this study, Alinia® tablets administered 500 mg twice daily with food for 24 weeks produced virologic responses (undetectable serum HCV RNA) in 7 of 23 patients (30.4%) compared to zero of 25 patients (0%) from the placebo group (P=0.0039). The virologic responses occurred between 4 and 20 weeks of treatment (3 at week 4, 3 at week 8, 1 at week 20) and were maintained through the end of treatment with no virological breakthroughs. Virologic response was sustained in 5 patients at least 24 weeks after the end of treatment.

Low viral load was the most significant independent predictor of virologic response (P=0.0086). None of the patients with cirrhosis, uncontrolled diabetes mellitus or hepatitis B virus co-infection responded to treatment.

When patients with high viral loads, cirrhosis, uncontrolled diabetes or hepatitis B co-infection were excluded from the efficacy analysis, virologic response rates were 7/10 (70%) for the active treatment group and 0/15 for the placebo group (P=0.0002). Two of the three Alinia®-treated failures included in this analysis had advanced liver disease with bridging fibrosis.

These results indicate that 24 weeks of Alinia monotherapy is effective in achieving a sustained virologic response in patients with chronic hepatitis C genotype 4 when the patients have low viral loads and no other complicating factors such as cirrhosis, uncontrolled diabetes or hepatitis B co-infection.

No safety concerns were identified during the course of the study. Adverse events reported for patients in the Alinia® treatment group were similar to those reported for the placebo group. There were no significant changes in clinical laboratory values over the 24-week course of treatment for the Alinia® treatment group compared to the placebo group.

Example 6

Treatment of Viral Hepatitis with Alinia and Pegylated Interferon Alpha-2B

Figure 6:
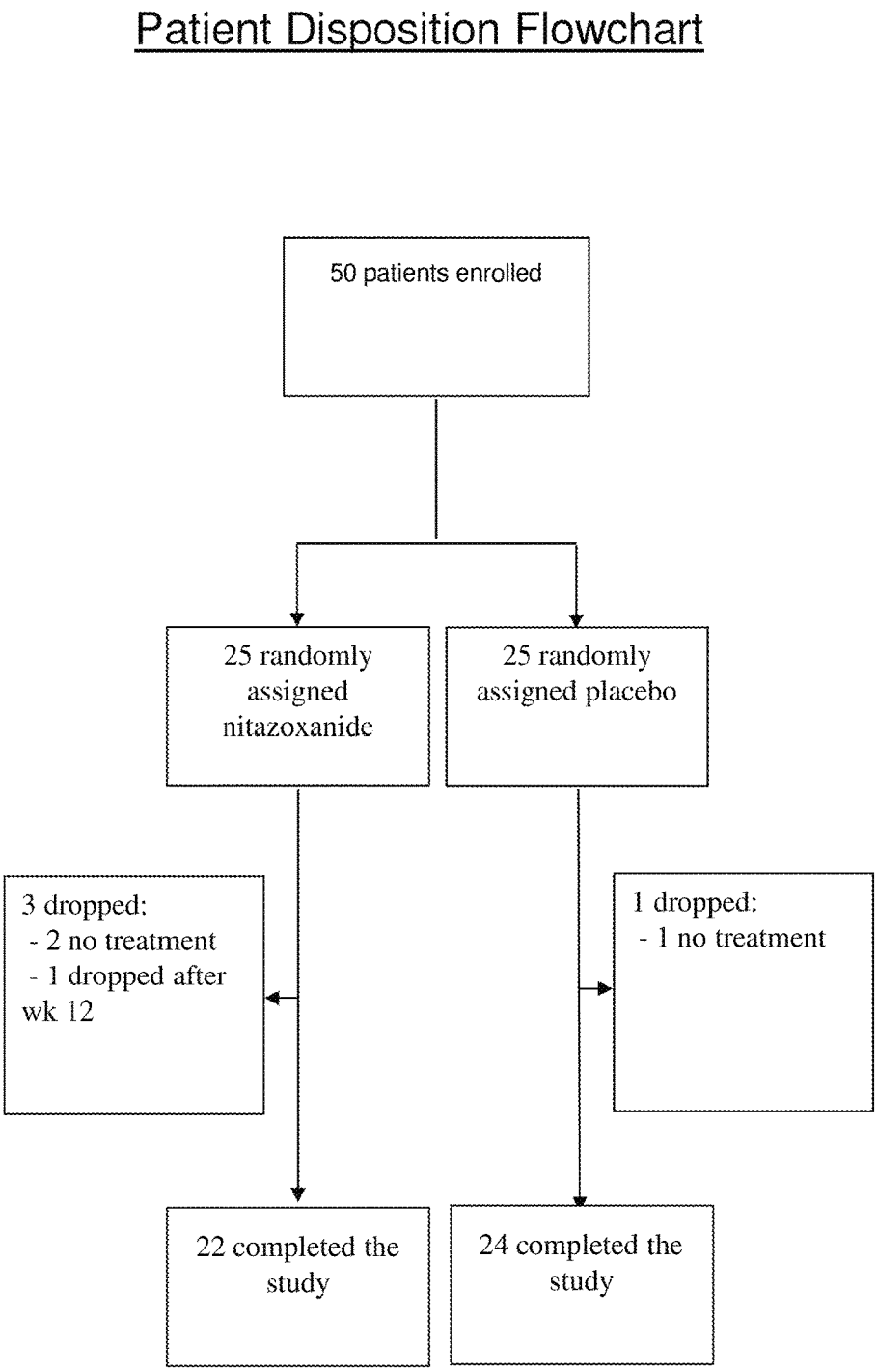
FIG. 6 is a patient disposition chart showing the selection of participants for the experiment described in Example 6.

Thirty-six (36) patients were enrolled in a clinical study to evaluate the effectiveness and safety of combination therapy with Alinia® plus pegylated interferon alpha-2b (PegIFN α-2b) compared to a placebo plus PegIFN α-2b in treating chronic hepatitis C. The patients were recruited as follows: Upon completing the 24-week treatment phase of study RM01-3027 (see Example 4), a randomized double-blind placebo-controlled study of Alinia®, eighteen (18) non-responders were offered the opportunity to participate in this clinical trial. Two patients declined enrollment due to the advanced stage of their disease and unwillingness to be treated with pegylated interferon. Sixteen (16) patients were enrolled in the study. These patients continued their blinded oral study medication along with 12 weekly injections of PegIFN α-2b. Twenty (20) treatment-naïve patients were recruited for the study to initiate blinded study medication plus PegIFN α-2b at the same time (first PegIFN injection and first dose of oral blinded medication on the same day). See FIG. 6 for a Patient Disposition Flowchart. One patient was enrolled with HCV genotype 2 (randomized to the pre-treated active group). One patient dropped out of the study immediately after receiving his first dose of PegIFN and did not return for any post-treatment follow-up. One patient did not return for follow-up after week 8. Each of the remaining 34 patients completed the study. An intent-to-treat population (all patients randomized) was used for the primary efficacy analysis with drop-outs being treated as failures. Demographic data and disease-related characteristics are summarized by treatment group in Table 20.

TABLE 20

Demographic and Disease-Related Characteristics

| | Pre-Treated | | Not Pre-Treated | | |
|---|---|---|---|---|---|
| | Active | Placebo | Active | Placebo | P[1] |
| Race: | | | | | |
| Caucasian | 8 | 8 | 10 | 10 | 1.0 |
| Gender: | | | | | |
| Male/Female | 8/0 | 7/1 | 8/2 | 10/0 | .20 |
| Age (years): | | | | | |
| Mean ± SD | 45.1 ± 5.5 | 41.3 ± 10.1 | 46.0 ± 9.1 | 39.1 ± 8.9 | .28 |
| Median (Range) | 46.5 (38-52) | 42.5 (27-55) | 48 (26-56) | 40 (21-49) | |
| Weight (kgs): | | | | | |
| Mean ± SD | 77.8 ± 6.6 | 84.0 ± 13.0 | 77.1 ± 11.8 | 77.7 ± 9.7 | .51 |
| Median (Range) | 79.5 (68-86) | 86 (67-105) | 79.5 (56-100) | 75 (64-94) | |
| Body Mass Index | | | | | |
| Mean ± SD | 26.0 ± 2.3 | 28.3 ± 4.5 | 26.1 ± 3.4 | 26.8 ± 3.8 | .54 |
| Median (Range) | 26.3 (21-29) | 29.0 (22-36) | 27.0 (20-31) | 25.7 (21-36) | |
| Viral load ($\log_{10}$ IU/mL)[2] | | | | | |
| Mean ± SD | 5.5 ± 0.6 | 5.6 ± 0.5 | 5.9 ± 0.5 | 5.6 ± 0 .4 | .34 |
| Median (Range) | 5.6 (4.3-6.1) | 5.6 (4.9-6.5) | 5.9 (4.9-6.6) | 5.7 (4.5-6.1) | |
| Viral load ≥800,000 IU/mL | 3 (38%) | 2 (25%) | 4 (40%) | 1 (10%) | .39 |
| Elevated ALT | 7 (88%) | 7 (88%) | 9 (90%) | 8 (80%) | .95 |
| Advanced liver disease | | | | | |
| Cirrhosis | 1 (13%) | — | — | 1 (10%) | .34 |
| Bridging fibrosis | 2 (25%) | 1 (13%) | — | — | |
| Diabetes mellitus | 3 (38%) | 1 (13%) | 1 (10%) | 1 (10%) | .42 |

[1]Chi-square test used for comparing proportions, analysis of variance for means.
[2]For pre-treated patients, viral loads are presented as determined before the pre-treatment period.

Each of the weekly peginterferon injections were administered by the physicians. At each study visit, patients were questioned regarding compliance with administration of the oral study medication (Alinia or placebo). With the exception of one patient who dropped out of the study during the first week and another patient who did not return for evaluation at week 12 and was treated as a nonresponder, each of the patients reported that they had been compliant with taking the medication. None of the patients returned unused medication.

Virologic responses are summarized by treatment group in Table 21. The response rate for the pre-treated active group (5/8, 63%) was higher than that of the pre-treated placebo group (P=0.15734), non-pretreated active group (P=0.08824), the non-pretreated placebo group (P=0.31859), the two placebo groups combined (P=0.16888) and the three other groups combined (P=0.09102).

TABLE 21

| Virologic Responses by Treatment Group | Pre-treated | | Not Pre-treated | |
|---|---|---|---|---|
| | Active | Placebo | Active | Placebo |
| Responders/ Total (%) | 5/8 (63%) | 2/8 (25%) | 2/10 (20%) | 4/10 (40%) |

P = 0.26, chi-square test

Logistic regression analyses identified lower fasted blood glucose as a significant independent predictor of virologic response (P=0.0101) for the entire population of patients studied (n=36). The relationship between fasted blood glucose and virologic response was most significant (P=0.0011) in the pre-treated active group where there were three patients with uncontrolled diabetes mellitus.

Given the relationships observed between virologic response and fasted blood glucose, the efficacy analysis was repeated for a subset of patients which excluded patients with uncontrolled diabetes mellitus. The results of this analysis are presented in Table 5. In this subset of non-diabetic patients, the response rate for the pre-treated active group (5/5, 100%) was higher than that of the pre-treated placebo group (P=0.02652), non-pretreated active group (P=0.01049), the non-pretreated placebo group (P=0.06294), the two placebo groups combined (P=0.02270) and the three other groups combined (P=0.00903). Demographic and disease-related characteristics of the subset of non-diabetic patients analyzed in Table 22 were compared by treatment group, and there were no significant differences between groups.

TABLE 22

| Virologic Responses by Treatment Group, Excluding Patients with Uncontrolled Diabetes Mellitus | Pre-Treated | | Not Pre-Treated | |
|---|---|---|---|---|
| | Active | Placebo | Active | Placebo |
| Responders/ Total (%) | 5/5 (100%) | 2/7 (29%) | 2/9 (22%) | 4/9 (44%) |

P = 0.01, chi-square test

Each of the virologic responders in the pre-treated Alinia®+pegIFN group had complicating disease-related factors that might ordinarily reduce the probability of treatment success with pegIFN-ribavirin. Response rates for subsets of patients with high viral loads, advanced liver disease, and uncontrolled diabetes are presented by treatment group in Table 23.

TABLE 23

| Response Rates in Patients with Complicating Disease-Related Factors | No. Responders/Total | | | |
|---|---|---|---|---|
| | Pre-Treated | | Not Pre-Treated | |
| | Active | Placebo | Active | Placebo |
| Viral load >800,000 IU/mL | 2/2 | 0/1 | 1/3 | 0/1 |
| Advanced liver disease: | | | | |
| Cirrhosis | 1/1 | — | — | — |
| Bridging fibrosis | 1/1 | 1/1 | — | — |

TABLE 23-continued

| Response Rates in Patients with Complicating Disease-Related Factors | No. Responders/Total | | | |
|---|---|---|---|---|
| | Pre-Treated | | Not Pre-Treated | |
| | Active | Placebo | Active | Placebo |
| HBV co-infection | 1/1 | — | — | — |
| Uncontrolled diabetes | 0/2 | — | — | — |
| with high viral load (HVL) | — | 0/1 | 0/1 | — |
| with HVL and bridging fibrosis | 0/1 | — | — | — |
| with cirrhosis | — | — | — | 0/1 |
| None of the above | — | 1/5 | 1/6 | 4/8 |

Two-log drop in serum HCV RNA. All patients with a 2-log drop in serum HCV RNA at the end of treatment also had undetectable serum HCV RNA. The results are, therefore, the same as presented in Tables 21, 22, and 23.

Changes in ALT from baseline to week 12 are summarized by treatment group in Table 24.

TABLE 24

| Changes in ALT by Treatment Group | Pre-Treated | | Not Pre-Treated | |
|---|---|---|---|---|
| | Active | Placebo | Active | Placebo |
| Normalized | 3 | 1 | 2 | 2 |
| Remained Elevated | 4 | 6 | 6 | 4 |
| Remained Normal | 1 | 1 | 1 | 1 |
| Normal to Elevated | — | — | — | 1 |

Note:
3 patients not evaluable due to missing ALT data at either baseline or end of treatment.

Virologic responses by treatment group are presented for each of two study centers in Table 25. The same data is presented for the subset of patients without uncontrolled diabetes in Table 26. In the overall analysis, there was no significant difference between the response rates observed for the two study centers. In the subset analysis, the response rates were significantly different because the second study center had two patients that responded on placebo+pegIFN. These two patients were 27 and 30 year-old males with low viral loads and no complicating disease-related conditions. The patient enrolled in the non-pretreated active group with genotype 2 was a nonresponder. There were no other significant protocol deviations.

TABLE 25

| Virologic Responses by Study Site and Treatment Group | No. Responders/Total | | | |
|---|---|---|---|---|
| | Pre-treated | | Not Pre-treated | |
| | Active | Placebo | Active | Placebo |
| First study center | 3/5 | 0/5 | 2/10 | 4/10 |
| Second study center | 2/3 | 2/3 | — | — |

P = 0.35, Cochran-Mantel-Haenszel test

TABLE 26

| Virologic Responses by Study Site and Treatment Group, Patients without Uncontrolled Diabetes Mellitus | | | | |
|---|---|---|---|---|
| | No. Responders/Total | | | |
| | Pre-treated | | Not Pre-treated | |
| | Active | Placebo | Active | Placebo |
| First study center | 3/3 | 0/4 | 2/9 | 4/9 |
| Second study center | 2/2 | 2/3 | — | — |

P = 0.0465, Cochran-Mantel-Haenszel test

Administration of 24 weeks of Alinia® followed by 12 weeks of Alinia plus pegIFN alfa-2b produced higher virologic response rates (5/8, 63%) than either pegIFN alfa-2b plus placebo for 12 weeks (6/18, 33%) or Alinia® plus pegIFN alfa-2b for 12 weeks without pre-treatment (2/10, 20%).

When patients with uncontrolled diabetes mellitus were excluded, the response rate for the pre-treated active group (5/5, 100%) was higher than that of the pre-treated placebo group (2/7, 29%, P=0.02652), non-pretreated active group (2/9, 22%, P=0.01049), the non-pretreated placebo group (4/9, 44%, P=0.06294), the two placebo groups combined (6/16, 38%, P=0.02270) and the three other groups combined (8/25, 32%, P=0.00903).

Each of the 5 virologic responders in the pre-treated active treatment group had disease-related complications that might typically reduce the probability of success with pegIFN-ribavirin therapy: 2 with viral load>800,000 IU/mL, 2 with advanced liver disease (1 cirrhosis, 1 bridging fibrosis) and 1 with hepatitis B virus co-infection.

These results indicate that pre-treatment of patients with Alinia® before adding pegIFN potentiates the effect of pegIFN, producing response rates that are significantly higher than those for pegIFN alone or Alinia plus pegIFN without a pre-treatment period.

Drug safety measures were examined for patients treated with Alinia® plus pegIFN and for those receiving placebo plus pegIFN. The extent of exposure is summarized in Table 27.

TABLE 27

| Extent of Exposure | |
|---|---|
| Treatment/Exposure | No. of Patients |
| Alinia 500 mg twice daily × 12 weeks + weekly pegIFN injections | 18 |
| Placebo twice daily × 24 weeks + weekly pegIFN injections | 17 |
| One peginterferon injection (dropped out) | 1 |

Four mild adverse events (AEs) were reported, three for patients in the placebo treatment group and one for a patient in the active treatment group. There were no serious adverse events. None of the adverse events required modification or discontinuation of treatment. Adverse events are displayed by body system, standard term, severity and causality in Table 28 for the active treatment group and in Table 29 for the placebo treatment group. The proportions of patients reporting each adverse event were compared by treatment group. There were no significant differences in the frequency or nature of adverse events reported by the two treatment groups. No deaths, serious AEs, or other significant AEs were reported. No laboratory adverse events were reported during the study.

TABLE 28

| Adverse Events: Patients Exposed to Alinia (N = 18) | | | | | | | | | | | | | | |
|---|---|---|---|---|---|---|---|---|---|---|---|---|---|---|
| | Patients | | Severity and Relationship to Use of the Drug[2] | | | | | | | | | | | |
| Adverse event | Reporting AEs | | Mild | | | | Moderate | | | | Severe | | | |
| (Affected system)[1] | Number | % | N | U | P | PR | N | U | P | PR | N | U | P | PR |
| Depression (NER) | 1 | 5.6 | — | 1 | — | — | — | — | — | — | — | — | — | — |

[1]NER = Nervous system
[2]Relationship to use of the drug: N = not related, U = unlikely related, P = possibly related, PR = probably related

TABLE 29

| Adverse Events: Patients Exposed to Placebo (N = 17) | | | | | | | | | | | | | | |
|---|---|---|---|---|---|---|---|---|---|---|---|---|---|---|
| | Patients | | Severity and Relationship to Use of the Drug[2] | | | | | | | | | | | |
| Adverse event | Reporting AEs | | Mild | | | | Moderate | | | | Severe | | | |
| (Affected system)[1] | Number | % | N | U | P | PR | N | U | P | PR | N | U | P | PR |
| Petechia (HAL) | 1 | 5.8 | — | 1 | — | — | — | — | — | — | — | — | — | — |
| Depression (NER) | 1 | 5.8 | — | 1 | — | — | — | — | — | — | — | — | — | — |
| Photosensitivity (BODY) | 1 | 5.8 | — | 1 | — | — | — | — | — | — | — | — | — | — |

Figure 7:
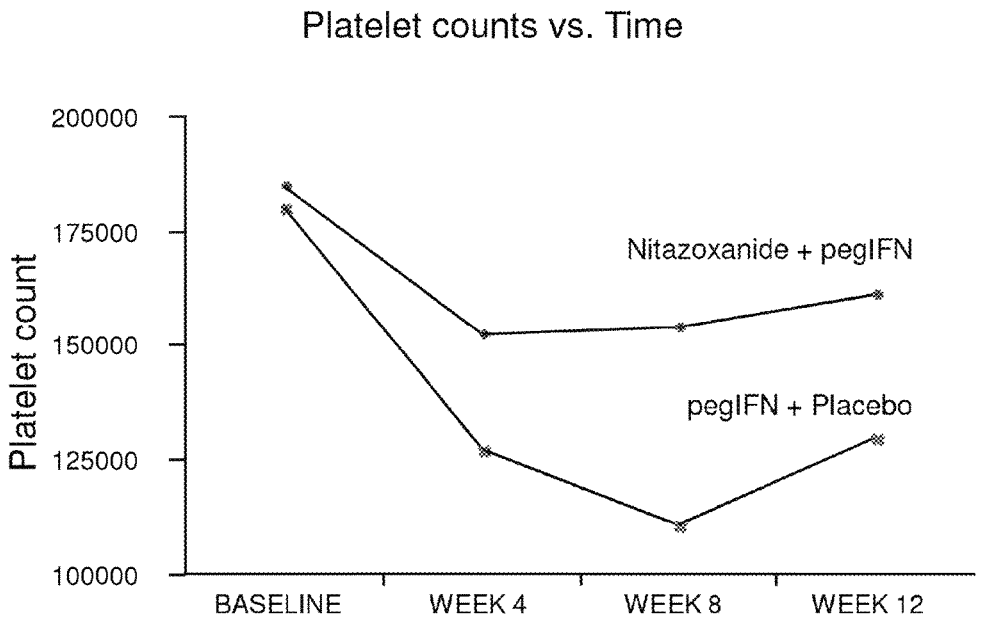
FIG. 7, described in Example 6, is a graph showing platelet count versus time for patients administered pegylated interferon alpha-2b plus either Alinia® or a placebo.
Figure 8:
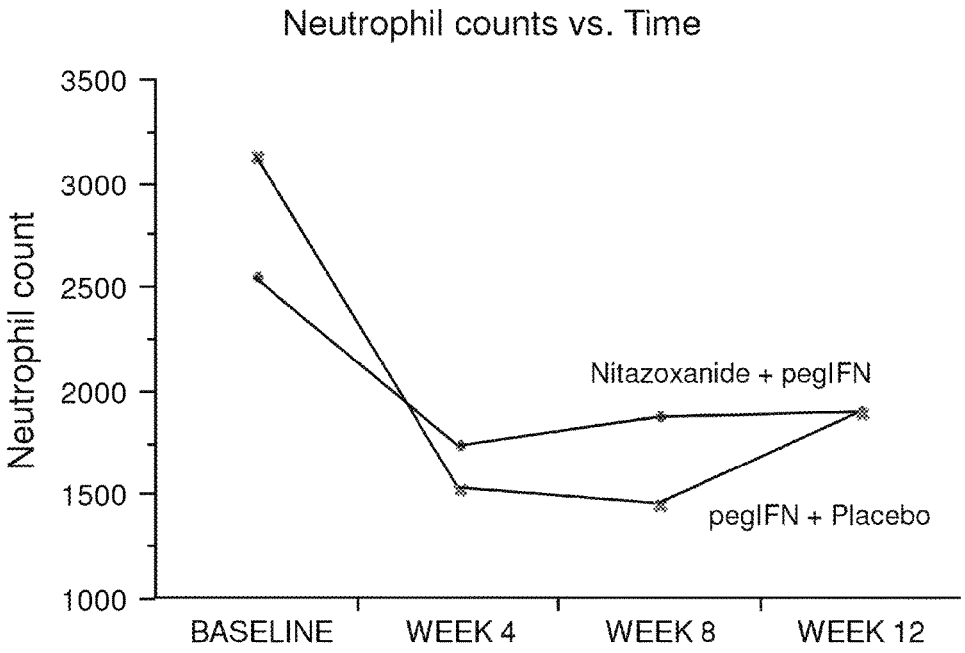
FIG. 8, described in Example 6, is a graph showing neutrophil count versus time for patients administered pegylated interferon alpha-2b plus either Alinia® or a placebo.

[1]HAL = Heme and Lymphatic System. NER = Nervous system. BODY = Body as a whole or Nonspecific system
[2]Relationship to use of the drug: N = not related, U = unlikely related, P = possibly related, PR = probably related Changes in laboratory safety parameters over time were analyzed by treatment group using repeated measures analysis of variance for continuous data and Fisher's Exact tests for categorical data. Significant differences were observed for two parameters: platelet counts over time were higher for the patients treated with Alinia+pegIFN than for patients treated with pegIFN+placebo (P=0.0138), as shown in FIG. 7; and absolute neutrophil counts over time were higher for patients treated with Alinia+pegIFN than for patients treated with pegIFN+placebo (P=0.0205), as shown for FIG. 8.

Values recorded for platelet counts and neutrophil counts increased from week 8 to week 12. A number of patients had their week 12 serum sample collected 3 to 7 days late (10 to 14 days after the last injection of pegIFN), and their platelet and neutrophil counts had begun to recover. To eliminate the effect of data collected late at week 12, data from baseline to week 8 was analyzed separately. When the week 12 data point was eliminated the differences in platelet counts and absolute neutrophil counts over time remained significant (P=0.0044 for platelets, P=0.0101 for neutrophils).

Analyses were conducted to evaluate the effect of virologic response or pre-treatment with Alinia on the change in platelet counts or neutrophil counts over time. The differences were not related to virologic response or pre-treatment with Alinia.

Vital signs, physical findings, and other observations related to safety provided no significant findings.

The administration of Alinia tablets administered 500 mg twice daily with food along with weekly injections of pegylated interferon alfa-2b for 12 weeks in patients with chronic hepatitis C was safe and well tolerated.

Reductions of platelet counts and neutrophil counts typically associated with administration of pegIFN were significantly smaller in patients treated with Alinia (P=0.0044 and 0.0101, respectively).

Administration of 24 weeks of Alinia followed by 12 weeks of Alinia plus pegIFN alfa-2b produced higher virologic response rates (5/8, 63%) than either pegIFN alfa-2b plus placebo for 12 weeks (6/18, 33%) or Alinia plus pegIFN alfa-2b for 12 weeks without pre-treatment (2/10, 20%).

When patients with uncontrolled diabetes mellitus were excluded, the response rate for the pre-treated active group (5/5, 100%) was higher than that of the pre-treated placebo group (2/7, 29%, P=0.02652), non-pretreated active group (2/9, 22%, P=0.01049), the non-pretreated placebo group (4/9, 44%, P=0.06294), the two placebo groups combined (6/16, 38%, P=0.02270) and the three other groups combined (8/25, 32%, P=0.00903).

Each of the 5 virologic responders in the pre-treated active treatment group had disease-related complications that might typically reduce the probability of success with pegIFN-ribavirin therapy: 2 with viral load>800,000 IU/mL, 2 with advanced liver disease (1 cirrhosis, 1 bridging fibrosis) and 1 with hepatitis B virus co-infection.

The administration of Alinia along with pegIFN alfa-2b in patients with chronic hepatitis C was safe and well tolerated. No safety concerns were identified.

Reductions of platelet counts and neutrophil counts typically associated with administration of pegIFN were significantly smaller in patients treated with Alinia (P=0.0044 and 0.0101, respectively).

These results indicate that pre-treatment of patients with Alinia before adding pegIFN potentiates the effect of pegIFN, producing response rates significantly higher than those for pegIFN alone or Alinia plus pegIFN without a pre-treatment period. Concomitant administration of Alinia may furthermore reduce the hematologic toxicity of pegIFN.

What is claimed is:

1. A method of treating hepatitis C in a patient suffering from hepatitis C, the method comprising administering to the patient a compound selected from nitazoxanide and tizoxanide or a mixture thereof, in an amount effective to reduce serum hepatitis C virus RNA in the serum of the patient to undetectable levels after administering the compound to the patient for a first period of time between about 3 days and about 24 weeks, wherein the amount is from 100 mg to 2000 mg per day.

2. The method of claim 1, wherein the compound is administered in the form of a composition further comprising a pharmaceutically acceptable carrier.

3. The method of claim 2, wherein the composition comprises a mixture of nitazoxanide and tizoxanide.

4. The method of claim 2, wherein the composition further comprises one or more additional biologically active agents selected from the group consisting of an interferon, an anti-diabetic agent, ribavirin and 2-methyl cytidine.

5. The method of claim 1 or 3, further comprising, after the first period of time, administering the compound or composition and an interferon to the patient for a second period of time of between about 1 week and about 48 weeks.

6. The method of claim 1, wherein the compound is administered to the patient for a period of between about 3 days and about 2 years.

7. The method of claim 1 or 3, wherein the method further comprises administering one or more additional active agents selected from the group consisting of an interferon, an anti-diabetic agent, ribavirin and 2-methyl cytidine.

8. The method of claim 7, wherein the one or more additional active agents comprises an interferon.

9. The method of claim 8, wherein the interferon is formulated separately from the compound.

10. The method of claim 8, wherein the interferon is interferon α-2a, interferon α-2b, or a polyethylene glycol conjugate of interferon α-2a or interferon α-2b.

11. The method of claim 8, wherein the interferon is administered to the patient for a period of about 1 week to about 48 weeks.

12. The method of claim 11, wherein the interferon is administered to the patient for a period of about 1 week to about 4-12 weeks.

13. The method of claim 8, wherein the interferon is administered to the patient between 1 and 3 times each week.

14. The method of claim 8, wherein administration of the interferon is initiated after the first period of time.

15. The method of claim 8, wherein the first period of time is between about 1 week and about 4 weeks.

16. The method of claim 1, wherein the compound is administered to the patient one to three times each day during the period of treatment.

17. The method of claim 7, wherein the one or more additional active agents comprises an anti-diabetes agent.

18. The method of claim 17, wherein the anti-diabetes agent is formulated separately from the compound.

19. The method of claim 4, wherein the composition comprises an anti-diabetes agent.

20. The method of claim 4, wherein the composition comprises an interferon.

21. The method of claim 4, wherein the composition comprises an interferon and an anti-diabetes agent.

22. A method of treating a patient suffering from hepatitis C, the method comprising (a) pretreating the patient for a predetermined period of time with an amount of nitazoxanide, tizoxanide or a mixture thereof, said amount being in the range of 100 mg to 2000 mg per day, and (b) after the predetermined period of time, administering to the patient an amount of an interferon, wherein the method is effective to reduce serum hepatitis C virus RNA in the serum of the patient to undetectable levels.

23. The method of claim 22, wherein the predetermined period of time is between about 3 days and about 3 months.

24. The method of claim 23, wherein the predetermined period of time is between about 1 week and about 4 weeks.

25. The method of claim 22, wherein interferon is selected from interferon α-2a, interferon α-2b, and a polyethylene glycol conjugate of interferon α-2a or interferon α-2b.

26. The method of claim 25, wherein step (b) further comprises administering a compound selected from nitazoxanide, tizoxanide or a mixture thereof.

*27. A method of treating liver fibrosis comprising administering to a subject in need thereof an effective amount of a compound selected from nitazoxanide, tizoxanide and a mixture thereof.*

*28. The method of claim 27, wherein the compound is administered in the form of a composition further comprising a pharmaceutically acceptable carrier.*

*29. The method of claim 28, wherein the composition comprises a mixture of nitazoxanide and tizoxanide.*

*30. The method of claim 27, wherein the fibrosis is caused by hepatitis.*

*31. The method of claim 30, wherein the hepatitis is hepatitis C.*

*32. The method of claim 27, wherein the effective amount is from about 100 mg to about 2000 mg per day.*

*33. The method of claim 27, wherein the effective amount is from 250 mg to 1000 mg per day.*

*34. The method of claim 27, wherein the effective amount achieves and maintains in the subject a blood level of tizoxanide between 0.1 μg/ml and 10 μg/ml.*

*35. The method of claim 27, wherein the compound is administered orally in an oral dosage form.*

*36. The method of claim 35, wherein the oral dosage form is a tablet, a capsule, a caplet or a particulate.*

*37. The method of claim 35, wherein the oral dosage form provides a sustained release of the compound over an extended period of time.*

*38. The method of claim 35, wherein the subject is a human.*

*39. The method of claim 27, wherein the fibrosis comprises fibrous portal expansion.*

*40. The method of claim 27, wherein the fibrosis is bridging fibrosis.*

*41. The method of claim 27, wherein said administering slows down progression of the fibrosis.*

* * * * *